US010897650B2

United States Patent
el Kaliouby et al.

(10) Patent No.: US 10,897,650 B2
(45) Date of Patent: *Jan. 19, 2021

(54) VEHICLE CONTENT RECOMMENDATION USING COGNITIVE STATES

(71) Applicant: Affectiva, Inc., Boston, MA (US)

(72) Inventors: Rana el Kaliouby, Milton, MA (US); Abdelrahman N. Mahmoud, Somerville, MA (US); Panu James Turcot, Pacifica, CA (US); Andrew Todd Zeilman, Beverly, MA (US); Gabriele Zijderveld, Somerville, MA (US)

(73) Assignee: Affectiva, Inc., Boston, MA (US)

( * ) Notice: Subject to any disclaimer, the term of this patent is extended or adjusted under 35 U.S.C. 154(b) by 123 days.

This patent is subject to a terminal disclaimer.

(21) Appl. No.: 16/211,592

(22) Filed: Dec. 6, 2018

(65) Prior Publication Data

US 2019/0110103 A1 Apr. 11, 2019

Related U.S. Application Data

(63) Continuation-in-part of application No. 15/875,644, filed on Jan. 19, 2018, which is a continuation-in-part (Continued)

(51) Int. Cl.
*H04N 21/466* (2011.01)
*H04N 21/4223* (2011.01)
(Continued)

(52) U.S. Cl.
CPC ....... *H04N 21/4668* (2013.01); *A61B 5/0022* (2013.01); *A61B 5/0077* (2013.01);
(Continued)

(58) Field of Classification Search
CPC ........ A61B 2503/22; A61B 2562/0204; A61B 2576/00; A61B 5/0022; A61B 5/0077;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Fasel, B. (Aug. 2002). Robust face analysis using convolutional neural networks. In Object recognition supported by user interaction for service robots (vol. 2, pp. 40-43). IEEE.
(Continued)

*Primary Examiner* — Babar Sarwar
(74) *Attorney, Agent, or Firm* — Adams Intellex, PLC

(57) ABSTRACT

Content manipulation uses cognitive states for vehicle content recommendation. Images are obtained of a vehicle occupant using imaging devices within a vehicle. The one or more images include facial data of the vehicle occupant. A content ingestion history of the vehicle occupant is obtained, where the content ingestion history includes one or more audio or video selections. A first computing device is used to analyze the one or more images to determine a cognitive state of the vehicle occupant. The cognitive state is correlated to the content ingestion history using a second computing device. One or more further audio or video selections are recommended to the vehicle occupant, based on the cognitive state, the content ingestion history, and the correlating. The analyzing can be compared with additional
(Continued)

analyzing performed on additional vehicle occupants. The additional vehicle occupants can be in the same vehicle as the first occupant or different vehicles.

26 Claims, 11 Drawing Sheets

Related U.S. Application Data of application No. 15/273,765, filed on Sep. 23, 2016, now abandoned, which is a continuation-in-part of application No. 14/796,419, filed on Jul. 10, 2015, now abandoned, application No. 16/211,592, which is a continuation-in-part of application No. 15/357,585, filed on Nov. 21, 2016, now Pat. No. 10,289,898, which is a continuation-in-part of application No. 14/821,896, filed on Aug. 10, 2015, now Pat. No. 9,503,786, and a continuation-in-part of application No. 15/262,197, filed on Sep. 12, 2016, now abandoned, said application No. 14/796,419 is a continuation-in-part of application No. 14/460,915, filed on Aug. 15, 2014, which is a continuation-in-part of application No. 13/153,745, filed on Jun. 6, 2011, said application No. 14/821,896 is a continuation-in-part of application No. 14/796,419, filed on Jul. 10, 2015, now abandoned, said application No. 14/821,896 is a continuation of application No. 13/406,068, filed on Feb. 27, 2012, now Pat. No. 9,106,958.

(60) Provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,449, filed on Dec. 1, 2017, provisional application No. 62/593,440, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/581,913, filed on Dec. 30, 2011, provisional application No. 61/580,880, filed on Dec. 28, 2011, provisional application No. 61/568,130, filed on Dec. 7, 2011, provisional application No. 61/549,560, filed on Oct. 20, 2011, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | | |
|---|---|---|
| *H04N 21/25* | (2011.01) | |
| *H04N 21/442* | (2011.01) | |
| *A61B 5/16* | (2006.01) | |
| *G06Q 30/06* | (2012.01) | |
| *G06N 3/00* | (2006.01) | |
| *G06K 9/00* | (2006.01) | |
| *B60W 40/08* | (2012.01) | |
| *G06N 20/10* | (2019.01) | |
| *G08G 1/0967* | (2006.01) | |
| *H04N 21/422* | (2011.01) | |
| *G10L 25/48* | (2013.01) | |
| *G08G 1/04* | (2006.01) | |
| *G08G 1/01* | (2006.01) | |
| *A61B 5/00* | (2006.01) | |
| *G06K 9/62* | (2006.01) | |
| *A61B 5/18* | (2006.01) | |
| *G06N 3/08* | (2006.01) | |
| *G06N 3/04* | (2006.01) | |

(52) U.S. Cl.
CPC ............... *A61B 5/165* (2013.01); *A61B 5/18* (2013.01); *A61B 5/6893* (2013.01); *A61B 5/742* (2013.01); *A61B 5/7405* (2013.01); *B60W 40/08* (2013.01); *G06K 9/00315* (2013.01); *G06K 9/00832* (2013.01); *G06K 9/6271* (2013.01); *G06N 3/006* (2013.01); *G06N 3/0454* (2013.01); *G06N 3/084* (2013.01); *G06N 20/10* (2019.01); *G06Q 30/0631* (2013.01); *G08G 1/012* (2013.01); *G08G 1/0112* (2013.01); *G08G 1/0116* (2013.01); *G08G 1/0129* (2013.01); *G08G 1/04* (2013.01); *G08G 1/096716* (2013.01); *G08G 1/096725* (2013.01); *G08G 1/096741* (2013.01); *G08G 1/096775* (2013.01); *G10L 25/48* (2013.01); *H04N 21/251* (2013.01); *H04N 21/4223* (2013.01); *H04N 21/42203* (2013.01); *H04N 21/44218* (2013.01); *H04N 21/44222* (2013.01); *H04N 21/4667* (2013.01); *A61B 2503/22* (2013.01); *A61B 2562/0204* (2013.01); *A61B 2576/00* (2013.01); *G06K 2009/00328* (2013.01); *G06N 3/0481* (2013.01); *H04N 21/4666* (2013.01)

(58) Field of Classification Search
CPC ......... A61B 5/165; A61B 5/18; A61B 5/6893; A61B 5/7405; A61B 5/742; B60W 40/08; G06K 2009/00328; G06K 9/00315; G06K 9/00832; G06K 9/6271; G06N 20/10; G06N 3/006; G06N 3/0454; G06N 3/0481; G06N 3/084; G06Q 30/0631; G08G 1/0112; G08G 1/0116; G08G 1/012; G08G 1/0129; G08G 1/04; G08G 1/096716; G08G 1/096725; G08G 1/096741; G08G 1/096775; G10L 25/30; G10L 25/48; G10L 25/63; H04N 21/251; H04N 21/42203; H04N 21/4223; H04N 21/44218; H04N 21/44222; H04N 21/4666; H04N 21/4667; H04N 21/4668

See application file for complete search history.

(56) References Cited

U.S. PATENT DOCUMENTS

| | | | |
|---|---|---|---|
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A | 11/1996 | Wildes et al. | |
| 5,619,571 A | 4/1997 | Sandstorm et al. | |
| 5,647,834 A | 7/1997 | Ron | |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,508 A | 6/1998 | Sugita et al. | |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,942,979 A * | 8/1999 | Luppino | B60K 28/066 180/272 |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,091,334 A | 7/2000 | Galiana et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,606,102 B1 | 8/2003 | Odom | |
| 6,629,104 B1 | 9/2003 | Parulski et al. | |
| 6,724,920 B1 | 4/2004 | Berenz et al. | |
| 6,792,458 B1 | 9/2004 | Muret et al. | |
| 6,847,376 B2 | 1/2005 | Engeldrum et al. | |
| 7,003,135 B2 | 2/2006 | Hsieh et al. | |
| 7,013,478 B1 | 3/2006 | Hendricks et al. | |
| 7,027,621 B1 | 4/2006 | Prokoski | |
| 7,110,570 B1 | 9/2006 | Berenz et al. | |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,779 B1 | 1/2008 | Mummareddy et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,757,171 B1 | 7/2010 | Wong et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |
| 8,022,831 B1 | 9/2011 | Wood-Eyre | |
| 8,219,438 B1 | 7/2012 | Moon et al. | |
| 8,300,891 B2 | 10/2012 | Chen et al. | |
| 8,369,608 B2 | 2/2013 | Gunaratne | |
| 8,401,248 B1 | 3/2013 | Moon et al. | |
| 8,442,638 B2 | 5/2013 | Libbus et al. | |
| 8,522,779 B2 | 9/2013 | Lee et al. | |
| 8,600,120 B2 | 12/2013 | Gonion et al. | |
| 8,640,021 B2 | 1/2014 | Perez et al. | |
| 8,738,523 B1 | 5/2014 | Sanchez et al. | |
| 8,947,217 B2 | 2/2015 | Moussa et al. | |
| 10,289,898 B2 * | 5/2019 | el Kaliouby | A61B 5/165 |
| 10,401,860 B2 * | 9/2019 | Krupat | G06K 9/4652 |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1 * | 5/2003 | Dimitrova | H04N 7/18 725/10 |
| 2003/0182123 A1 | 9/2003 | Mitsuyoshi | |
| 2003/0191682 A1 | 10/2003 | Shepard et al. | |
| 2003/0191816 A1 | 10/2003 | Landress et al. | |
| 2004/0039483 A1 * | 2/2004 | Kemp | G05B 13/0265 700/245 |
| 2004/0181457 A1 | 9/2004 | Biebesheimer | |
| 2005/0187437 A1 | 8/2005 | Matsugu | |
| 2005/0283055 A1 | 12/2005 | Shirai et al. | |
| 2005/0289582 A1 | 12/2005 | Tavares et al. | |
| 2006/0011399 A1 | 1/2006 | Brockway et al. | |
| 2006/0019224 A1 | 1/2006 | Behar et al. | |

(56) References Cited

U.S. PATENT DOCUMENTS

| | | |
|---|---|---|
| 2006/0143647 A1* | 6/2006 | Bill ............... G06F 16/683 725/10 |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0201227 A1* | 8/2008 | Bakewell ........ G06Q 30/0217 705/14.19 |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0144071 A1* | 6/2009 | Saito ............... G06Q 30/0281 705/346 |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0036717 A1* | 2/2010 | Trest ............... G06Q 30/0266 705/14.1 |
| 2010/0070523 A1 | 3/2010 | Delgo et al. |
| 2010/0099955 A1* | 4/2010 | Thomas ............ H04L 12/1827 600/300 |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0087971 A1* | 4/2011 | Kamrani ............ G06Q 10/06 715/752 |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0108266 A1* | 5/2012 | Clark .............. H04W 4/029 455/456.3 |
| 2012/0109452 A1 | 5/2012 | Autran et al. |
| 2012/0324491 A1 | 12/2012 | Bathiche et al. |
| 2013/0023337 A1 | 1/2013 | Bowers et al. |
| 2013/0030645 A1* | 1/2013 | Divine ............... B60K 35/00 701/36 |
| 2013/0116587 A1 | 5/2013 | Sornmo et al. |
| 2013/0197409 A1 | 8/2013 | Baxter et al. |
| 2013/0204455 A1 | 8/2013 | Chia et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2015/0258995 A1 | 9/2015 | Essers et al. |
| 2016/0104486 A1 | 4/2016 | Penilla et al. |
| 2017/0003784 A1 | 1/2017 | Garg et al. |
| 2018/0143635 A1* | 5/2018 | Zijderveld ......... G05D 1/0221 |
| 2018/0144649 A1* | 5/2018 | el Kaliouby ......... G09B 5/06 |
| 2018/0196432 A1* | 7/2018 | Krupat .............. G10L 15/1815 |
| 2018/0330178 A1* | 11/2018 | el Kaliouby ....... G06K 9/00228 |
| 2019/0162549 A1* | 5/2019 | Fouad ............... G08G 1/0129 |
| 2019/0197330 A1* | 6/2019 | Mahmoud ........... B60W 40/08 |
| 2019/0268660 A1* | 8/2019 | el Kaliouby ....... G06K 9/00845 |
| 2019/0283762 A1* | 9/2019 | el Kaliouby ........ G06N 3/08 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

Matsugu, M., Mori, K., Mitari, Y., & Kaneda, Y. (2003). Subject independent facial expression recognition with robust face detection using a convolutional neural network. Neural Networks, 16(5-6), 555-559.

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

* cited by examiner

VEHICLE CONTENT RECOMMENDATION USING COGNITIVE STATES

RELATED APPLICATIONS

This application claims the benefit of U.S. provisional patent applications "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State" Ser. No. 62/679,825, filed Jun. 3, 2018.

This application is also a continuation-in-part of U.S. patent application "Video Recommendation Via Affect" Ser. No. 15/357,585, filed Nov. 21, 2016, which claims the benefit of U.S. provisional patent applications "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Video Recommendation Via Affect" Ser. No. 15/357,585, filed Nov. 21, 2016 is also a continuation-in-part of U.S. patent application "Video Recommendation Using Affect" Ser. No. 14/821,896, filed Aug. 10, 2015, which is a continuation-in-part of U.S. patent application "Video Recommendation Based on Affect" Ser. No. 13/406,068, filed Feb. 27, 2012, which claims the benefit of U.S. provisional patent applications "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertising" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011.

The patent application "Video Recommendation Via Affect" Ser. No. 15/357,585, filed Nov. 21, 2016 is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Vehicle Manipulation using Occupant Image Analysis" Ser. No. 15/875,644, filed Jan. 19, 2018 which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524, 606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicle Manipulation using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370, 421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796, 419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF INVENTION

This application relates generally to content manipulation and more particularly to vehicle content recommendation using cognitive states.

BACKGROUND

People who are traveling experience a wide diversity of cognitive states. The people may be operating, riding in, or supervising a given vehicle. The purposes for the travel vary extensively. Some people travel to commute to work or school, for pleasure or discovery, or for exercise, among many other purposes. Other travelers are unwilling ones, fleeing famine, natural disasters, war, or economic displacement. Modes of transportation include ground, water, and air transportation. Travelers choose a transportation mode based on availability, cost, convenience, or the purpose of the travel. Whichever transportation mode is chosen, people spend a consequential amount of time traveling.

Waiting for, traveling in, or parking the vehicle, waiting in security lines to get on the vehicle, among many other travel related activities, all consume or waste time. Travel is at best a long process, and at worst, boring and vexatious. Time expended traveling or commuting is time lost from productive activities such as work, study, art, family, and so on. Rush hour traffic, accidents, and poorly maintained roads further complicate vehicle transportation. Travel difficulties are exacerbated by operating an unfamiliar vehicle, traveling in an unfamiliar city, or even having to remember to drive on the opposite side of the road. Failure to address these transportation realities can have catastrophic consequences. Irritated vehicle operators can experience road rage and other strongly antisocial behaviors. Bored, sleepy, impaired, distracted, or inattentive drivers can precipitate vehicular accidents that cause damage to property and tragically, can cause injury to themselves or other vehicle occupants, pedestrians, bicyclists, pets, or wild animals

SUMMARY

In disclosed techniques, vehicle content recommendation uses cognitive states based on analysis of images and other data of a vehicle occupant. The vehicle content that can be recommended can include audio or video selections, where the audio or video selections may be recommended from a library, a stream, and so on. One or more in-vehicle imaging devices are used to collect images of a vehicle occupant, where the images include facial data. The vehicle can be a first vehicle, a second vehicle, a third vehicle, a public transportation vehicle, etc. The images can include images based on various light spectra such as visible light images or near-infrared (NIR) images. Other in-vehicle sensors can be used such as a microphone for collecting audio data or voice data, and other sensors to collect physiological data. A content ingestion history of the vehicle occupant can be obtained, where the content ingestion history includes one or more audio or video selections. The content ingestion history can be obtained based on a user identifier, data collected during prior trips in the vehicle or vehicles, etc. A first computing device is used to analyze the one or more images to determine a cognitive state of the vehicle occupant. The computing device can be a device within the vehicle, an electronic device used by an occupant of the vehicle, a computing device such as a server beyond the vehicle, and the like. The cognitive state can be correlated to the content ingestion history using a second computing device. The cognitive state can include drowsiness, fatigue, distraction, impairment, sadness, stress, happiness, anger, frustration, etc. One or more further audio or video selections are recommended to the vehicle occupant, based on the cognitive state, the content ingestion history, and the correlating. The recommending can occur while the vehicle occupant occupies the vehicle or the recommending can occur after the vehicle occupant leaves the vehicle. The recommending can include comparing the analyzing with additional analyzing performed on additional vehicle occupants.

In embodiments, a computer-implemented method for content manipulation comprises: obtaining one or more images of a vehicle occupant using one or more imaging devices within a vehicle, wherein the one or more images include facial data of the vehicle occupant; obtaining a content ingestion history of the vehicle occupant, wherein the content ingestion history includes one or more audio or video selections; analyzing, using a first computing device, the one or more images to determine a cognitive state of the vehicle occupant; correlating the cognitive state to the content ingestion history using a second computing device; and recommending to the vehicle occupant one or more further audio or video selections, based on the cognitive state, the content ingestion history, and the correlating.

In some embodiments, the method further includes obtaining audio information from the occupant of the vehicle and augmenting the analyzing based on the audio information. The audio information can include speech, non-speech vocalizations, and so on. The non-speech vocalizations can include grunts, yelps, squeals, snoring, sighs, laughter, filled pauses, unfilled pauses, or yawns. Further embodiments include obtaining physiological information from the occupant of the vehicle and augmenting the analyzing based on the physiological information. The physiological information can include heart rate, heart rate variability, respiration rate, skin conductivity, and so on. The occupant of the vehicle can be a driver or operator of the vehicle, a passenger within the vehicle, a custodial driver of the vehicle, etc. The vehicle in which the individual is traveling can be an autonomous vehicle or a semi-autonomous vehicle.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
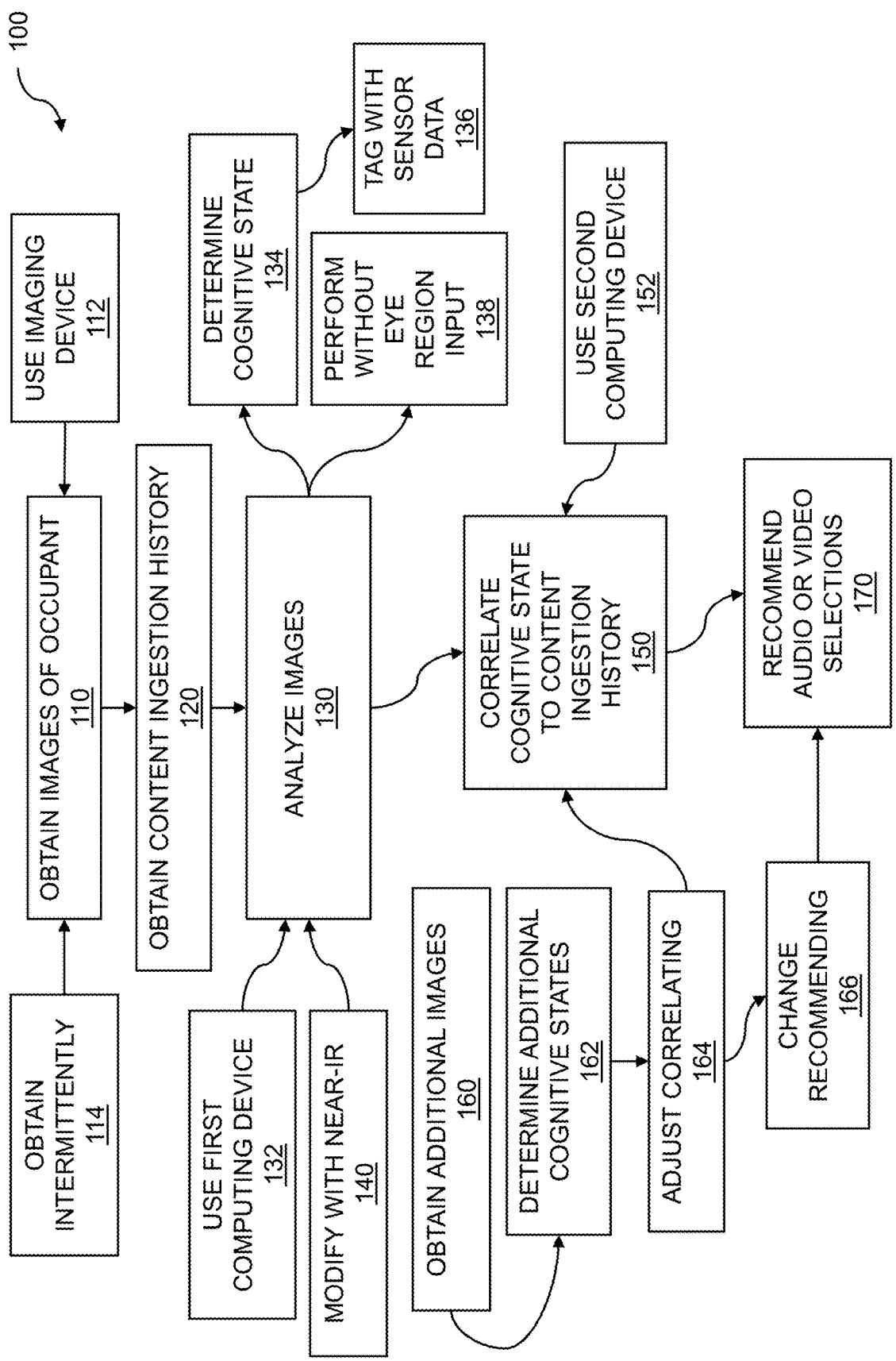
FIG. 1 is a flow diagram for vehicle content recommendation using cognitive states.

Individuals can choose to reside in areas as diverse as sparsely populated rolling hills or densely populated cities. Those individuals, whether they live in urban, suburban, or rural areas, spend hundreds or more hours per year traveling in vehicles. The vehicles that are most frequently used for travel include public, private, or commercial vehicles, such as buses, trains, airplanes, automobiles, ride share vehicles, and so on. The hours that individuals are spending in vehicles are consumed by commuting to and from work, running errands, meeting appointments, traveling, etc. As an individual is traveling within or atop a vehicle, that individual can experience a wide range of cognitive states. The type and range of cognitive states can be determined by analyzing cognitive state data collected from the individual. The cognitive state data that is analyzed can include image data, facial data, audio data, voice data, speech data, non-speech vocalizations, physiological data, and the like. In addition to the analysis of the cognitive state data from images, audio, etc., a history of content ingestion can be obtained from the vehicle occupant. The ingestion history can include one or more audio or video selections that were made by the vehicle occupant, offered to the vehicle occupant, and so on. The cognitive state can be correlated to the content ingestion history. The correlating can include a cognitive state such as "happy" occurring when a particular audio or video selection was playing.

In the disclosed techniques, content manipulation uses cognitive states of one or more occupants of a vehicle. Content manipulation can include vehicle content recommendation. The vehicle content recommendation can include recommending one or more audio or video selections to one or more occupants of the vehicle. The vehicle content recommendation can be performed for a variety of purposes including setting or adjusting the cognitive state or states of one or more vehicle occupants. The cognitive state or states can be based on those states of a single vehicle occupant, aggregated cognitive state or states of multiple occupants of the vehicle, and so on. Images of a vehicle occupant are obtained using one or more imaging devices within a vehicle. The imaging devices can include cameras, where the cameras can include a video camera, a still camera, a camera array, a plenoptic camera, a web-enabled camera, a visible light camera, a near-infrared (NIR) camera, a heat camera, and so on. The obtained images include facial data of the vehicle occupant. A content ingestion history of the vehicle occupant is obtained, where the content ingestion history includes one or more audio or video selections. The content ingestion history can include a history of audio or video selection during a current trip in a vehicle, a past trip in the vehicle, trips in other vehicles, and the like. A first computing device is used to analyze the one or more images to determine a cognitive state of the vehicle occupant. The computing device can include an on-board computer, an electronic device used by the vehicle occupant, a server located beyond the vehicle, etc. The cognitive states can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state can be correlated to the content ingestion history using a second computing device. The second computing device and the first computing device can be the same computing device or different computing devices. Recommendations for further audio or video selections can be made to the vehicle occupant. The recommending can be based on the cognitive state, the content ingestion history, and the correlating.

FIG. 1 is a flow diagram for vehicle content recommendation using cognitive states. Vehicle content recommendation correlates one or more cognitive states to a content ingestion history of a vehicle occupant. Obtained images include facial data of a vehicle occupant. The images are analyzed using a first computing device to determine a cognitive state. An obtained content ingestion history includes one or more audio or video selections. The cognitive state is mapped to the content ingestion history using a second computing device. One or more further audio or video selections are recommended to the vehicle occupant based on the cognitive state, the content ingestion history, and the correlating.

The flow 100 includes obtaining one or more images of a vehicle occupant 110 using one or more imaging devices 112 within a vehicle. The one or more images that are obtained include facial data of the vehicle occupant. The images can include one or more light spectra such as visible light, near-infrared light, and so on. In embodiments, at least one of the one or more images can include near-infrared content. The one or more imaging devices within the vehicle can include any of a variety of cameras or other image capture devices suitable for image-based analysis. A camera can include a webcam, a video camera, a still camera, a thermal imager, a near infrared (NIR) camera, a CCD device, a phone camera, a three-dimensional camera, a depth camera, a light field camera, multiple webcams used to show different views of a person, or any image capture device. A camera or image capture device can capture light of various wavelengths. In embodiments, a wavelength of the near infrared light can be less than 950 nm. Other types of data can be collected of a vehicle occupant. In some embodiments, audio information is collected in place of images or in addition to images to augment the cognitive state data contained therein. Further data types of the vehicle occupant may be collected. In embodiments, physiological information from the occupant of the vehicle is collected in place of images or audio information, or in addition the images or audio information. The physiological data can be used to augment the analyzing. The vehicle occupant can be the driver of the vehicle, the operator of the vehicle, a passenger of the vehicle, etc. The vehicle can be an automobile, a bus, a van, a truck, a train, an airplane, a ship, etc. Other embodiments include intermittent obtaining of images 114 that include facial data. The intermittent obtaining of images can occur when a vehicle occupant is facing an imaging device, and not when the vehicle occupant is facing away from the imaging device.

The flow 100 includes obtaining a content ingestion history 120 of the vehicle occupant. The content ingestion history can include one or more audio or video selections. The audio or video selections can be made by the vehicle occupant during their current trip, a previous trip or trips, and so on. The content ingestion history can be based on a user identifier (UID), a user profile, anonymously data collected by an app on an electronic device associated with the vehicle operator, etc. The flow 100 includes analyzing 130 the one or more images. The analyzing includes using a first computing device 132. The first computing device can include a computing device within the vehicle, a smartphone, a personal digital assistant (PDA), a tablet computer, a laptop computer, etc., associated with the vehicle occupant. The first computing device can include a server located within the vehicle, a computing device located beyond the vehicle, etc. A computing device located beyond the vehicle can include a server, a remote server, a blade server, a cloud-based server, a mesh server, or the like. The analyzing the images includes determining a cognitive state 134 of the vehicle occupant. One or more cognitive states can be determined based on one or more algorithms, heuristics, procedures, codes, etc., for analysis. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Further to analyzing, the cognitive state data can be tagged. Further embodiments include tagging the cognitive state with sensor data 136. The tagging the cognitive state can be based on other data such as data collected relating to a vehicle, the exterior of the vehicle, the interior of the vehicle, and so on. In embodiments, the sensor data can include one or more of vehicle interior temperature, vehicle exterior temperature, time of day, day of week, season, level of daylight, weather conditions, road conditions, traffic conditions, headlight activation, windshield wiper activation, vehicle settings, entertainment center selection, and entertainment center volume. The analyzing of the of the one or more images including facial data can include analyzing a face, regions of a face, and so on. In embodiments, the analyzing is performed without eye region input 138 from the one or more images. The eye region input may not be available because one or both eyes of the vehicle occupant can be obscured by hair, a hat, dark glasses, an eyepatch, and the like. In embodiments, at least one of the one or more images includes near-infrared content. In embodiments, the analyzing is modified, based on the near-infrared (N-IR) content 140 of the at least one of the one or more images. The N-IR content can indicate that the vehicle occupant is flushed because she feels unwell or embarrassed, is overly warm due to vehicle climate settings, etc.

The flow 100 includes correlating the cognitive state to the content ingestion history 150. The correlating the cognitive state to the content ingestion history can be accomplished using a second computing device 152. Various algorithms, codes, procedures, and the like, can be used for the correlating. In embodiments, the correlating can be based on matching a cognitive state that was analyzed in an image to an audio or video selection that was playing contemporaneously with the cognitive state. The flow 100 further includes obtaining additional images 160 of one or more additional occupants of the vehicle. In embodiments, the additional vehicle occupants can occupy the vehicle contemporaneously with the vehicle occupant. The additional images can be obtained using one or more imaging devices within the same vehicle as the first vehicle occupant or can use other imaging devices. In embodiments, the additional vehicle occupants can occupy one or more different vehicles from the vehicle of the vehicle occupant. The additional images can be obtained using imaging devices within the additional vehicles. In the flow 100, the additional images are analyzed to determine one or more additional cognitive states 162. The additional cognitive states may be substantially similar to the one or more cognitive states of the first vehicle occupant or can be different from the cognitive states of the first vehicle occupant. The flow 100 includes adjusting the correlating 164 cognitive state, wherein the adjusting is performed using the additional cognitive states. The adjusting can be based on substantially similar cognitive states, on different cognitive states, on intensities of cognitive states, and the like. In embodiments, the occupant and the one or more additional occupants comprise a group of occupants and the adjusting is performed based on a group cognitive state.

The flow 100 includes recommending to the vehicle occupant one or more further audio or video selections 170. The recommending of the one or more further audio or video selections is based on the cognitive state, the content ingestion history, and the correlating. In embodiments, the recommending can occur while the vehicle occupant occupies the vehicle. The recommending can include recommending a favorite song to help the vehicle occupant feel happy; a calming song to reduce stress; a loud or raucous selection to dispel drowsiness; and so on. If the vehicle occupant is a passenger, the recommending can include a news or sport selection, a favorite rock video, a movie to pass the time, etc. In other embodiments, the recommending can occur after the vehicle occupant leaves the vehicle. The recommending can be made for the benefit of other individuals who remain in the vehicle after the first individual has left the vehicle. The flow 100 further includes changing the recommending 166 based on the adjusting. The changing the recommending can include recommending a song liked by the first vehicle occupant and the additional vehicle occupants. The recommending can include providing other audio including news, weather statements, emergency announcements, and the like.

Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
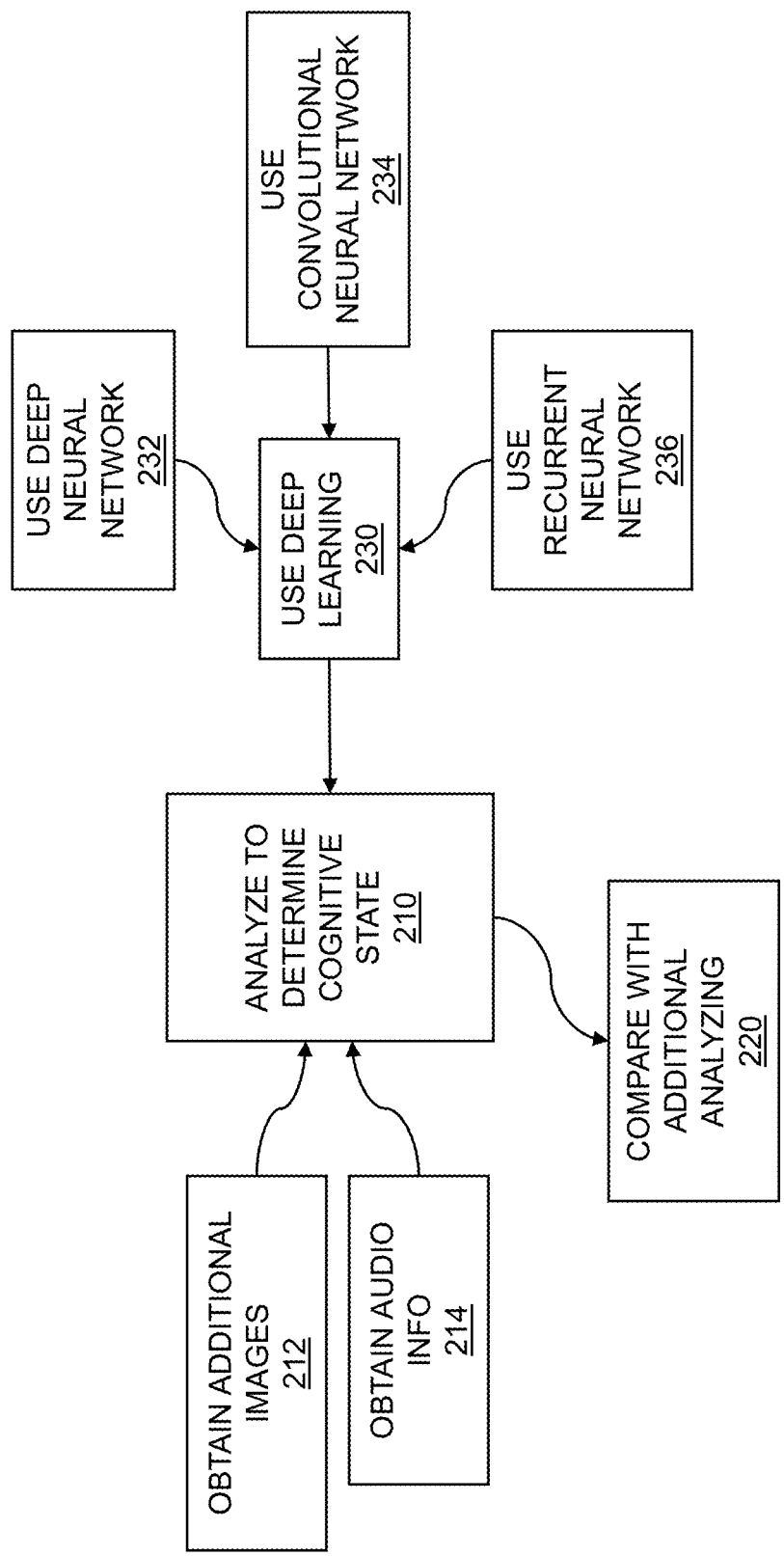
FIG. 2 is a flow diagram for further cognitive state analysis.

FIG. 2 is a flow diagram for further cognitive state analysis. Additional cognitive state data such as images, audio information, physiological information, and so on, can be obtained and analyzed to determine a cognitive state. The further cognitive state analysis supports vehicle content recommendation using cognitive states. The cognitive state or states can be correlated to a content ingestion history of a vehicle occupant using a computing device. The content ingestion history can include one or more audio or video selections made by the vehicle occupant. The computing device can include an on-vehicle computing device, an electronic device such as a smartphone or tablet computer associated with the vehicle occupant, and so on. The computing device can include a computing device located beyond the vehicle, where the computing device can include a computing device in another vehicle, a server, a blade server, a cloud server, a mesh server, and the like. One or more further audio or video selections are recommended to the vehicle occupant, based on the cognitive state, the content ingestion history, and the correlating.

The flow 200 includes obtaining additional images 212 of one or more additional occupants of the vehicle, where the additional images are analyzed 210 to determine one or more additional cognitive states. Images of the one or more additional occupants of the vehicle can be obtained using imaging devices within a vehicle. The images can include visible light images, near-infrared images, or images comprising other spectra, where the images of any type include facial data. The additional vehicle occupants can occupy the vehicle contemporaneously with the vehicle occupant. The additional vehicle occupants can include one or more passengers, a custodial driver, and the like. In embodiments, the additional vehicle occupants can occupy one or more different vehicles from the vehicle of the vehicle occupant. The other vehicle occupants can be operators or passengers in vehicles adjacent to the first vehicle occupants. The flow 200 includes obtaining audio information 214 from the occupant of the vehicle and augmenting the analyzing based on the audio information. The audio information can be obtained using a microphone, audio transducer, etc., where the microphone, for example, can be an in-vehicle microphone, a microphone coupled to an electronic device associated with a vehicle occupant, etc. The microphone can obtain a variety of audio information such as in-vehicle sounds, exterior sounds such as road noise, wind noise, or traffic noise, etc. In embodiments, the audio information can include speech. The speech information can include speech from the occupant of the vehicle, speech detected in an audio source such as a radio or streaming station, and the like. In other embodiments, the audio information can include non-speech vocalizations. The non-speech vocalizations can include a variety of human generated sounds. In embodiments, the non-speech vocalizations can include grunts, yelps, squeals, snoring, sighs, laughter, filled pauses, unfilled pauses, or yawns.

The flow 200 includes comparing the analyzing with additional analyzing 220 performed on additional vehicle occupants. The comparing the analyzing can be used to determine an average cognitive state, an aggregate cognitive state, a range of cognitive states, and so on. The comparing can be used to determine whether the vehicle occupant is experiencing a cognitive state similar to the other vehicle occupants or a different cognitive state. The additional cognitive states that can be determined by analyzing the additional images of the additional vehicle occupants can be used for adjusting the correlating the cognitive state. In embodiments, the flow can include obtaining physiological information from the occupant of the vehicle and augmenting the analyzing based on the physiological information. The physiological information can be inferred from image data or audio data, collected using cameras or sensors, and so on. The physiological information can include heart rate, heart rate variability, respiration rate, skin conductivity, and the like.

The flow 200 includes analyzing, where the analyzing is performed using deep learning 230. Deep learning can be based on learning one or more representations related to data, rather than relying on algorithms that can be specific to a given data analysis task. Data representations, such as those based on feature learning, include techniques for automating the discovery, by a deep learning system, of representations that can be used to classify or detect features in raw data. In embodiments, the learning is performed using a deep neural network 232. A deep neural network can include an input layer, an output layer, and hidden layers internal to the neural network. A deep learning network can use weights, biases, and layers that can be learned as part of training the deep neural network. A deep neural network can include a feed-forward network, in which data such as training data or raw data can flow from an input layer, through the neural network, to an output layer. In other embodiments, the learning is performed using a convolutional neural network (CNN) 234. A convolutional neural network can include properties such as space invariance, shift invariance, or translation invariance, which are properties that are particularly useful for image analysis. A CNN can require little preprocessing of input data because the CNN can learn filters. The learning the filters can obviate the need to code the filters. The filters can enhance image classification tasks such as facial data analysis. In further embodiments, the learning is performed using a recurrent neural network 236. A recurrent neural network (RNN) can include connections between nodes to form a directed graph. The directed graph can be along a sequence. An RNN can exhibit temporal behavior by using storage internal to the RNN to process input data sequences. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
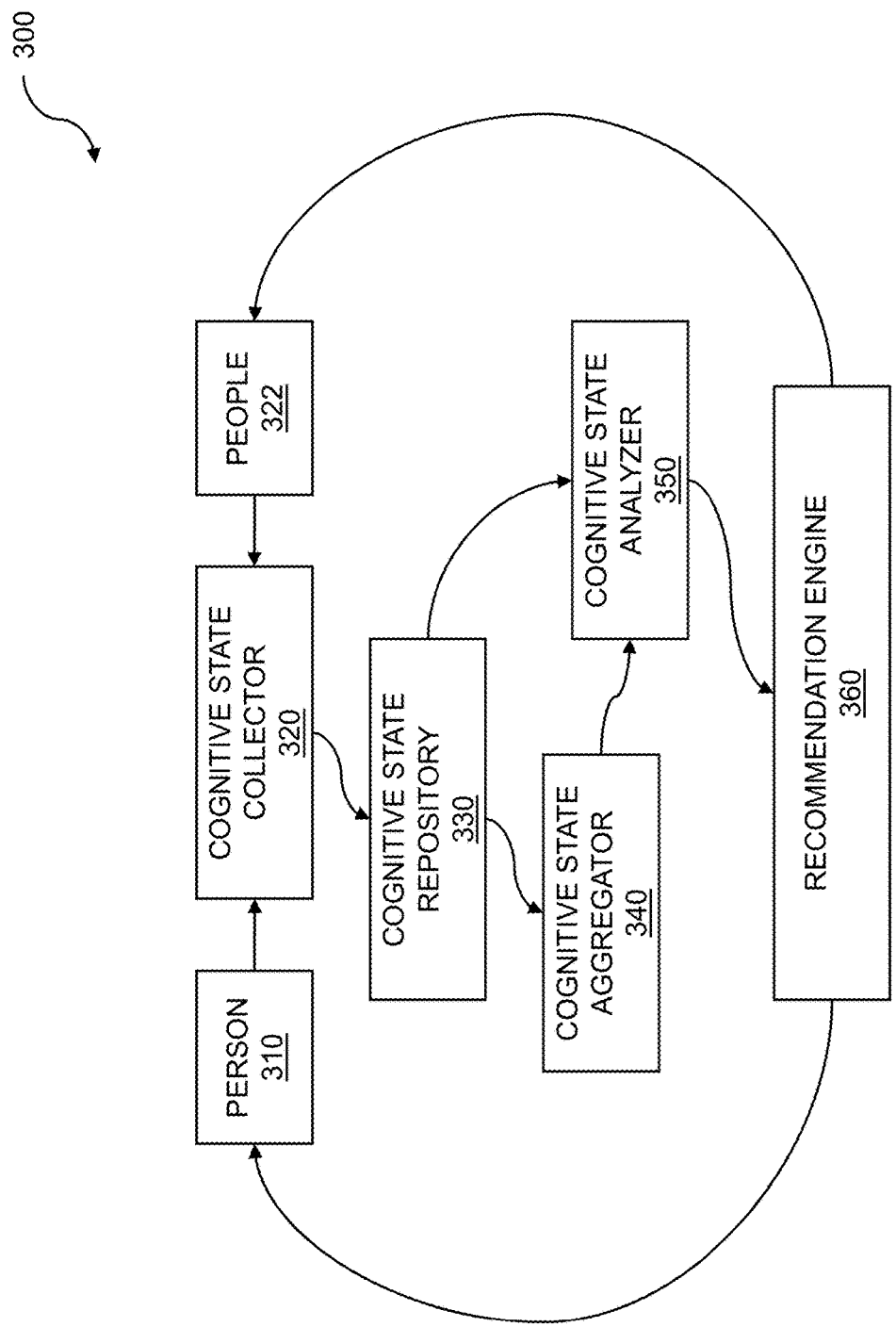
FIG. 3 is a diagram of a recommendation system.

FIG. 3 is a diagram of a recommendation system. The recommendation system can be used for vehicle content recommendation using cognitive states. Images of a vehicle occupant are obtained using one or more imaging devices within a vehicle. The one or more images include facial data of the vehicle occupant. A content ingestion history that includes one or more audio or video selections is obtained of the vehicle occupant. A first computing device is used to analyze the one or more images to determine a cognitive state of the vehicle occupant. The cognitive state is correlated to the content ingestion history using a second computing device. One or more further audio or video selections are recommended to the vehicle occupant, based on the cognitive state, the content ingestion history, and the correlating In the flow 300, a person 310 can view a video. While the person 310 is viewing a video, a cognitive state collector 320 can gather cognitive state data on the person 310. The cognitive state collector 320 can be a webcam or another camera device. The cognitive state collector 320 can be a biosensor attached to the person 310 in one or more locations. The cognitive state data collected from the person 310 by the cognitive state collector 320 can be stored in a cognitive state repository 330. The cognitive state repository 330 can be on a local computer or on a remote server, or it can be distributed as part of a cloud computing system.

A cognitive state analyzer 350 can analyze the cognitive state data collected from the person 310. The cognitive state analyzer 350 can recognize mental states including information on concentration, liking, disliking, etc. The cognitive state analyzer 350 can recognize smiles or frowns. Based on the analysis done by the cognitive state analyzer 350, a recommendation engine 360 can recommend a video or another media presentation to the person 310. The recommending of a media presentation to an individual can be based on the mental state data which was aggregated. The aggregated data can be for multiple videos by an individual, or it can be for a plurality of people. The recommendation can be based on common factors with one or more videos which the person 310 watched. For example, if the person 310 smiled for each of the videos that he or she watched that featured a specific actress as the main character, then the recommendation engine 360 can recommend another video with the same actress to the person 310. In another example, if a series of sports videos is liked by the person 310, then another sports video can be recommended.

Other people 322 can view the same video as the person 310. In some embodiments, multiple videos are viewed by the person 310 and the other people 322. In embodiments, different subsets of the multiple videos are viewed by each person. The cognitive state collector 320 can capture cognitive state data for each of the people 322. The cognitive state collector 320 can be a single unit such as a kiosk in a mall or a device which collects cognitive state for multiple people viewing a video in such a location as a conference room or a movie theater. Alternatively, the cognitive state collector 320 can be separate devices, if, for instance, each person has their own computer, laptop, cell phone, mobile device, or the like. The cognitive state repository 330 can retain cognitive state data from the people on whom cognitive state data is collected.

A cognitive state aggregator 340 can take cognitive state data from the cognitive state repository 330 and correlate cognitive state data from the person 310 with the other people 322. The cognitive state aggregator 340 can recognize trends for the person 310 who has watched multiple videos such as movies. The cognitive state aggregator 340 can determine correlation vectors for the person 310 and the people 322 or a subset thereof. A correlation can be made using weighted Euclidean or Mahalanobis distance evaluation between two vectors, where a vector includes an individual's cognitive state data. There are many ways to compute distances or similarity/dissimilarity measures. Collaborative filtering or the like can be used to aid in matching cognitive state data between or among people. In some embodiments, a comparison is made based on the same content viewed by the person 310 and by individuals from the other people 322. When one vector is at a sufficiently small distance from another person's vector, then the cognitive state aggregator 340 will look for other content that has been smiled at or liked. This other content can be recommended by the recommendation engine 360 to the person 310 because there are assumed similarities based on the cognitive state data which was collected.

In some embodiments, the cognitive state aggregator 340 and the cognitive state analyzer 350 are used to review cognitive state data stored in the cognitive state repository 330 to compare cognitive state data collected on a new video with an historical database of cognitive state data for videos. The new video can be evaluated to determine how the video ranks against other videos. For example, the new video could be compared with a "top 100" list of videos to determine the relative number of smiles that the new video has in comparison to the "top 100" list of videos for which people smiled. In embodiments, a group of people view a new video and have cognitive state data collected. The cognitive state data collected for the people can be aggregated together. The aggregated cognitive state data for the new video can then be compared to the aggregated cognitive state data for other videos. This type of comparison could be used by developers of videos to rank and evaluate a new video which has been produced. Likewise, a buyer of advertising spots, for example, could evaluate a new video based on aggregated cognitive state data collected from a group of people. An emotion profile for the video could be generated and then compared with a "best of breed" set of videos by network studios, advertisers, or others with similar commercial interest.

In some cases, there may be good correlation for one type of video but not for another. For instance, a good correlation can be made for drama videos but a poor one for comedy videos. Based on that information, a recommendation can be made for another drama video. Collaborative filtering can be performed to identify good possibilities for correlation, and therefore areas where videos can be recommended.

The recommendation engine 360 can make recommendations to the person 310 on whom cognitive state was collected. The recommendation engine 360 can make the recommendations based on the correlation between the person 310 and the other people 322. Likewise, the recommendation engine 360 can make recommendations to one or more of the people 322 based on a video that was viewed by the person 310.

Cognitive load can include an amount of cognitive effort required by a vehicle occupant as the occupant travels within or atop the vehicle. Cognitive load can indicate how engaged, distracted, inattentive, etc., the vehicle occupant can be with tasks related to the vehicle. Cognitive load can be adjusted for vehicle manipulation using cognitive state engineering. A vehicle occupant who is operating the vehicle or traveling in the vehicle can experience a variety of cognitive states. The cognitive states experienced by the occupant can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth, etc. In addition to one or more cognitive states, the occupant can experience cognitive load. Cognitive load can include an amount of cognitive effort required of the occupant to perform various tasks within the vehicle. The tasks can include operating the vehicle, listening to audio, negotiating a travel route, maneuvering in traffic, and the like. The cognitive load can be determined by mapping a cognitive state to a loading curve. The loading curve can represent a continuous spectrum of cognitive state loading variation. The spectrum of cognitive state loading variation can include a range from very underloaded to very overloaded. Adjusting the cognitive load of the vehicle occupant using cognitive state engineering can improve vehicle operation safety, enhance the experience of the vehicle occupant, and the like.

Figure 4:
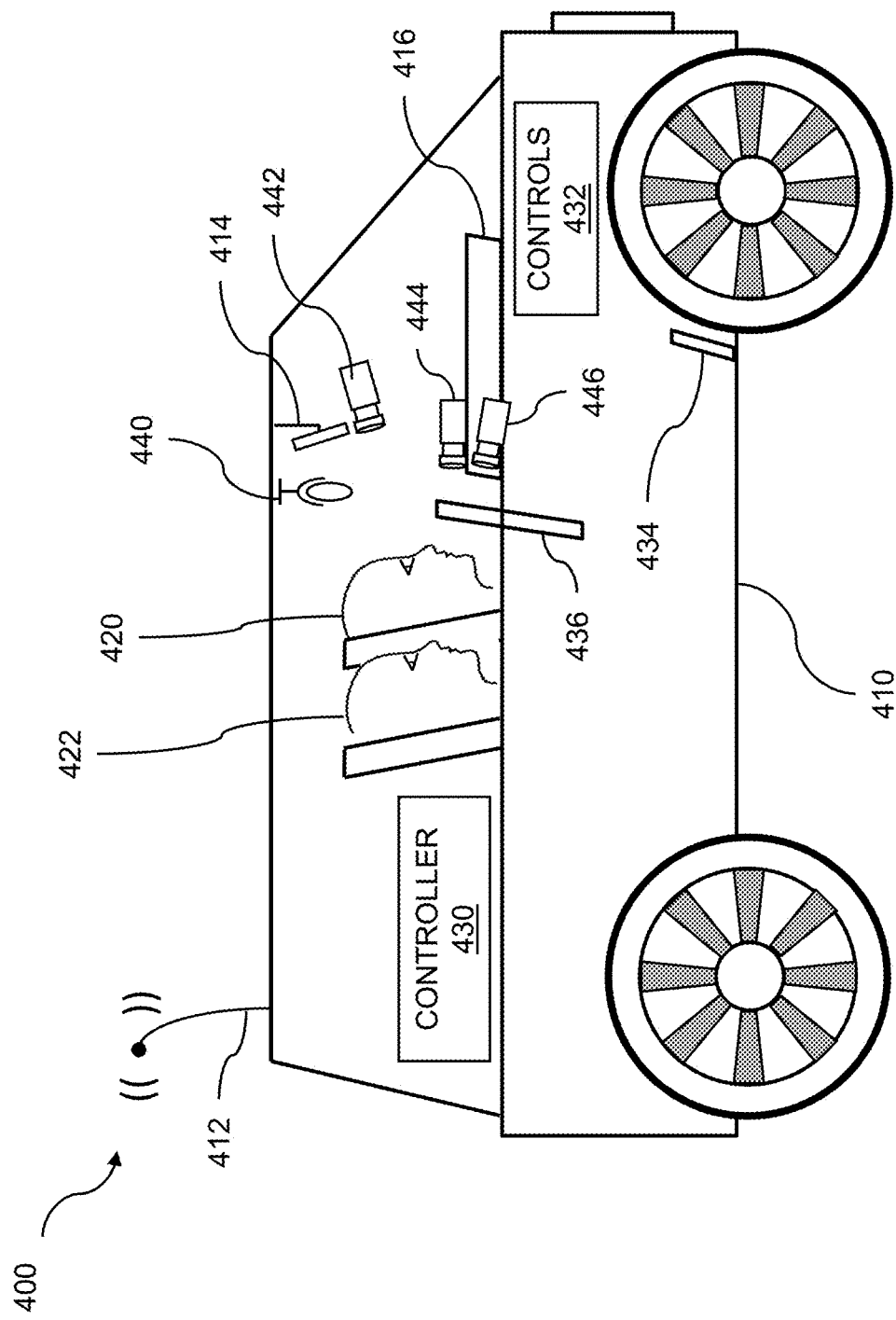
FIG. 4 is a system diagram for an interior of a vehicle.

FIG. 4 is a system diagram for an interior of a vehicle 400. Vehicle content recommendation can be based on cognitive states. Images including facial data of a vehicle occupant are obtained using one or more imaging devices within a vehicle. A content ingestion history, including audio or video selections, is obtained of the vehicle occupant. The images are analyzed to determine cognitive state, and the cognitive state is correlated to the content ingestion history. One or more further audio or video selections are made to the vehicle occupant, based on the cognitive state, the content ingestion history, and the correlating. One or more occupants of a vehicle 410, such as occupants 420 and 422, can be observed using a microphone 440, one or more cameras 442, 444, or 446, and other audio and image capture techniques. The image data can include video data. The video data and the audio data can include cognitive state data, where the cognitive state data can include facial data, voice data, physiological data, and the like. The occupant can be a driver 420 of the vehicle 410, a passenger 422 within the vehicle, a custodial driver of the vehicle (not shown) m and so on.

The cameras or imaging devices that can be used to obtain images including facial data from the occupants of the vehicle 410 can be positioned to capture the face of the vehicle operator, the face of a vehicle passenger, multiple views of the faces of occupants of the vehicle, and so on. The cameras can be located near a rear-view mirror 414 such as camera 442, positioned near or on a dashboard 416 such as camera 444, positioned within the dashboard such as camera 446, and so on. The microphone or audio capture device 440 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 410 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 410 can include standard controls such as a steering wheel 436, a throttle control (not shown), a brake 434, and so on. The interior of the vehicle can include other controls 432 such as controls for seats, mirrors, climate controls, audio systems, etc. The controls 432 of the vehicle 410 can be controlled by a controller 430. The controller 430 can control the vehicle 410 in various manners such as autonomously, semi-autonomously, assertively to a vehicle occupant 420 or 422, etc. In embodiments, the controller provides vehicle control or manipulation techniques, assistance, etc. The controller 430 can receive instructions via an antenna 412 or using other wireless techniques. The controller 430 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest route, and so on.

Figure 5:
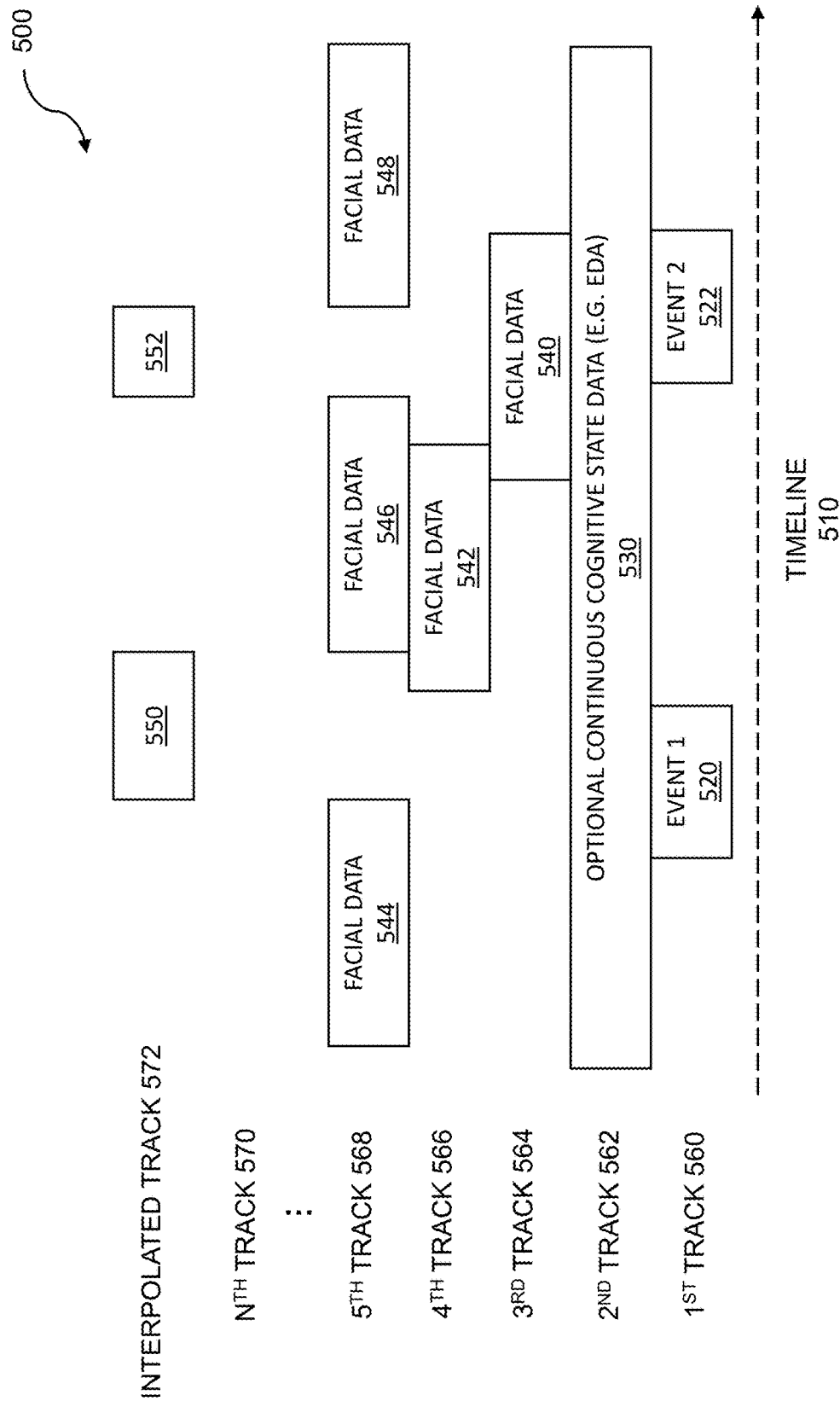
FIG. 5 is a timeline with information tracks relating to cognitive states.

FIG. 5 is a timeline with information tracks relating to cognitive states 500. A timeline can show one or more cognitive states that can be experienced by a vehicle occupant. The vehicle occupant can be an operator of the vehicle, a passenger of the vehicle, a custodial driver of the vehicle, and so on. The timeline can be based on vehicle content recommendation using cognitive states. Images including facial data of a vehicle occupant are obtained. A content ingestion history of the occupant is further obtained. The images are analyzed to determine a cognitive state, and the cognitive state is correlated to the content ingestion history. Further audio or video selections are recommended to the vehicle occupant based on the cognitive state, the content ingestion history, and the correlating.

The timeline 510 with information tracks 500 relates to various cognitive states. A first track 560 shows events that, in embodiments, are related to use of a computer by the individual. A first event 520 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 560. A second event 522 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 562 can include continuously collected cognitive state data such as electrodermal activity data 530. A third track 564 can include facial data. The facial data can be collected intermittently when the individual is looking toward a camera. The facial data 540 can include one or more still photographs, videos, or abstracted facial expressions which can be collected when the user looks in the direction of the camera. A fourth track 566 can include facial data that is collected either intermittently or continuously by a second camera. The facial data 542 can include one or more still photographs, videos, or abstracted facial expressions which can be collected when the user looks in the direction of that camera. A fifth track 568 can include facial data that is collected from a third camera, such as the webcam. In the example shown, the fifth track 568 includes first facial data 544, second facial data 546, and third facial data 548, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the n$^{th}$ track 570, of cognitive state data of any type can be collected. The additional tracks 570 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 572 can be included and can be associated with cognitive state data that is collected on an intermittent basis, such as the facial data of the fifth track 568. Interpolated data 550 and further interpolated data 552 can contain interpolations of the facial data of the fifth track 568 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 530 and/or any of the collected facial data 540, 542, 544, 546, and 548, can be tagged. The tags can include metadata related to the cognitive state data, including, but not limited to, the device that collected the cognitive state data; the individual from whom the cognitive state data was collected; the task being performed by the individual; the media being viewed by the individual; and the location, environ-cognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such, the tags can be used locally on the machine where the cognitive state data was collected and/or remotely on a remote server or a cloud/web service.

Other tags can be related to the cognitive state data, which is data related to, attached to, indicative of, including, containing, etc., the cognitive state. Further embodiments can include tagging the cognitive state data with sensor data. The sensor data can be obtained from the vehicle occupant along with the video data or the audio data, instead of the video data or the audio data, etc. In embodiments, the sensor data can include one or more of vehicle temperature, outside temperature, time of day, level of daylight, weather conditions, headlight activation, windshield wiper activation, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 6:
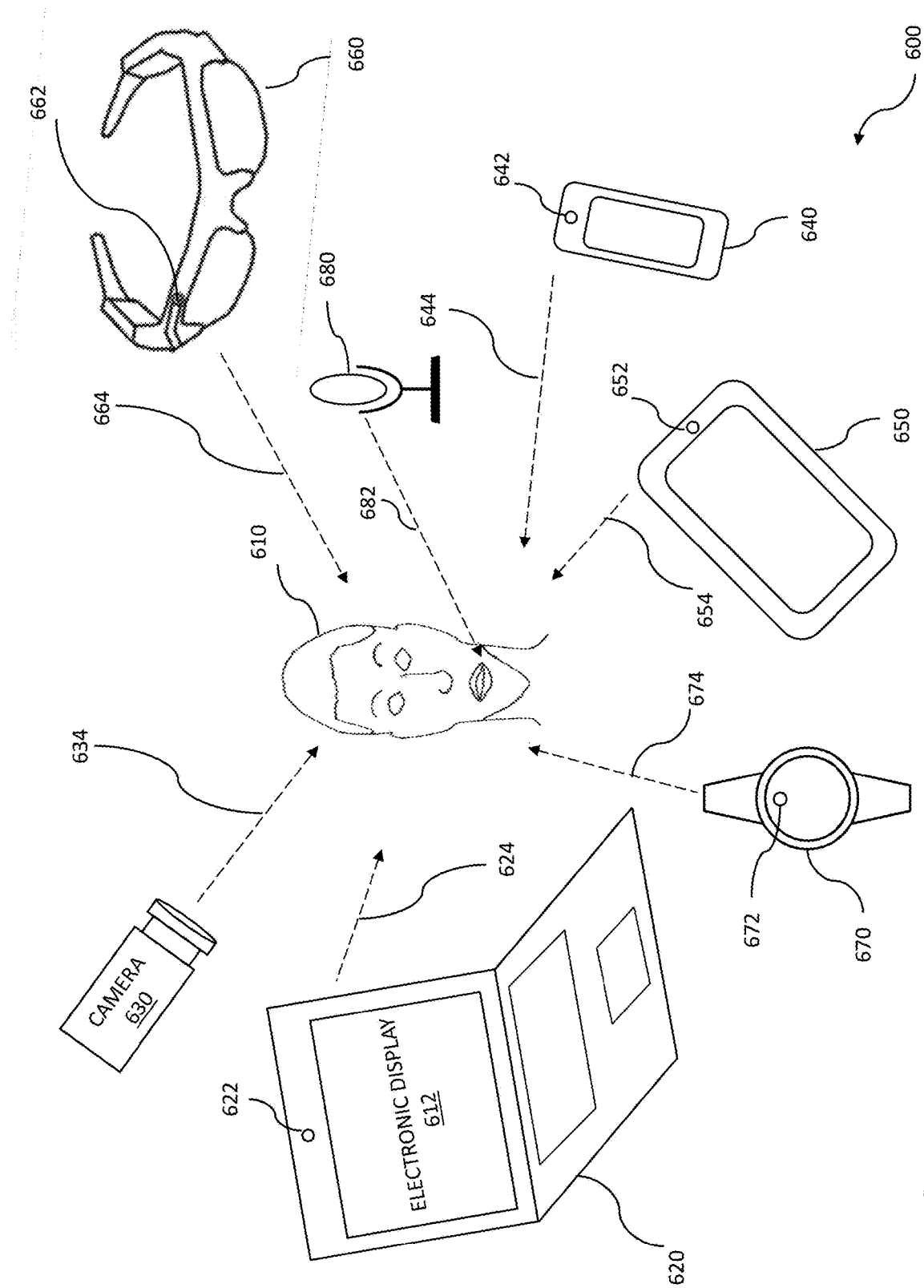
FIG. 6 shows example image and audio collection including multiple mobile devices.

FIG. 6 shows example image and audio collection including multiple mobile devices. Cognitive state data including image data, audio data, and physiological data, can be collected using multiple mobile devices. The collected cognitive state data can be used for vehicle content recommendation using cognitive states. Images including facial data of a vehicle occupant are obtained and analyzed to determine cognitive state. A history of content ingestion, including audio or video, is further obtained. The images are analyzed to determine a cognitive state, and the cognitive state is correlated to the content ingestion history. Further audio or video selections are recommended to the vehicle occupant, where the recommending is based on the cognitive state, the content ingestion history, and the correlating. While one person is shown, in practice the video, audio, physio, or other data on any number of people can be collected. In the diagram 600, the multiple mobile devices can be used separately or in combination to collect video data, audio data, physiological data, or some or all of video data, audio data, and physiological data, on a user 610. While one person is shown, the video data, audio data, or physiological data can be collected on multiple people. A user 610 can be observed as she or he is performing a task, experiencing an event, viewing a media presentation, and so on. The user 610 can be shown one or more media presentations, political presentations, social media, or another form of displayed media. The one or more media presentations can be shown to a plurality of people. The media presentations can be displayed on an electronic display 612 or another display. The data collected on the user 610 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 610 can be analyzed and viewed for a variety of purposes including expression analysis, cognitive state analysis, mental state analysis, emotional state analysis, and so on. The electronic display 612 can be on a laptop computer 620 as shown, a tablet computer 650, a cell phone 640, a television, a mobile monitor, or any other type of electronic device. In one embodiment, video data including expression data is collected on a mobile device such as a cell phone 640, a tablet computer 650, a laptop computer 620, or a watch 670. Similarly, the audio data including speech data and non-speech vocalizations can be collected on one or more of the mobile devices. Thus, the multiple sources can include at least one mobile device, such as a phone 640 or a tablet 650, or a wearable device such as a watch 670 or glasses 660. A mobile device can include a front-side camera and/or a back-side camera that can be used to collect expression data. A mobile device can include a microphone, audio transducer, or other audio capture apparatus that can be used to capture the speech and non-speech vocalizations. Sources of expression data can include a webcam 622, a phone camera 642, a tablet camera 652, a wearable camera 662, and a mobile camera 630. A wearable camera can comprise various camera devices, such as a watch camera 672. Sources of audio data 682 can include a microphone 680.

As the user 610 is monitored, the user might move due to the nature of the task, boredom, discomfort, distractions, or for another reason. As the user moves, the camera with a view of the user's face can be changed. Thus, as an example, if the user is looking in a first direction, the line of sight 624 from the webcam 622 is able to observe the user's face, but if the user is looking in a second direction, the line of sight 634 from the mobile camera 630 is able to observe the user's face. Furthermore, in other embodiments, if the user is looking in a third direction, the line of sight 644 from the phone camera 642 is able to observe the user's face, and if the user is looking in a fourth direction, the line of sight 654 from the tablet camera 652 is able to observe the user's face. If the user is looking in a fifth direction, the line of sight 664 from the wearable camera 662, which can be a device such as the glasses 660 shown and can be worn by another user or an observer, is able to observe the user's face. If the user is looking in a sixth direction, the line of sight 674 from the wearable watch-type device 670, with a camera 672 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 610 can also use a wearable device including a camera for gathering contextual information and/or collecting expression data on other users. Because the user 610 can move her or his head, the facial data can be collected intermittently when she or he is looking in a direction of a camera. In some cases, multiple people can be included in the view from one or more cameras, and some embodiments include filtering out faces of one or more other people to determine whether the user 610 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 7:
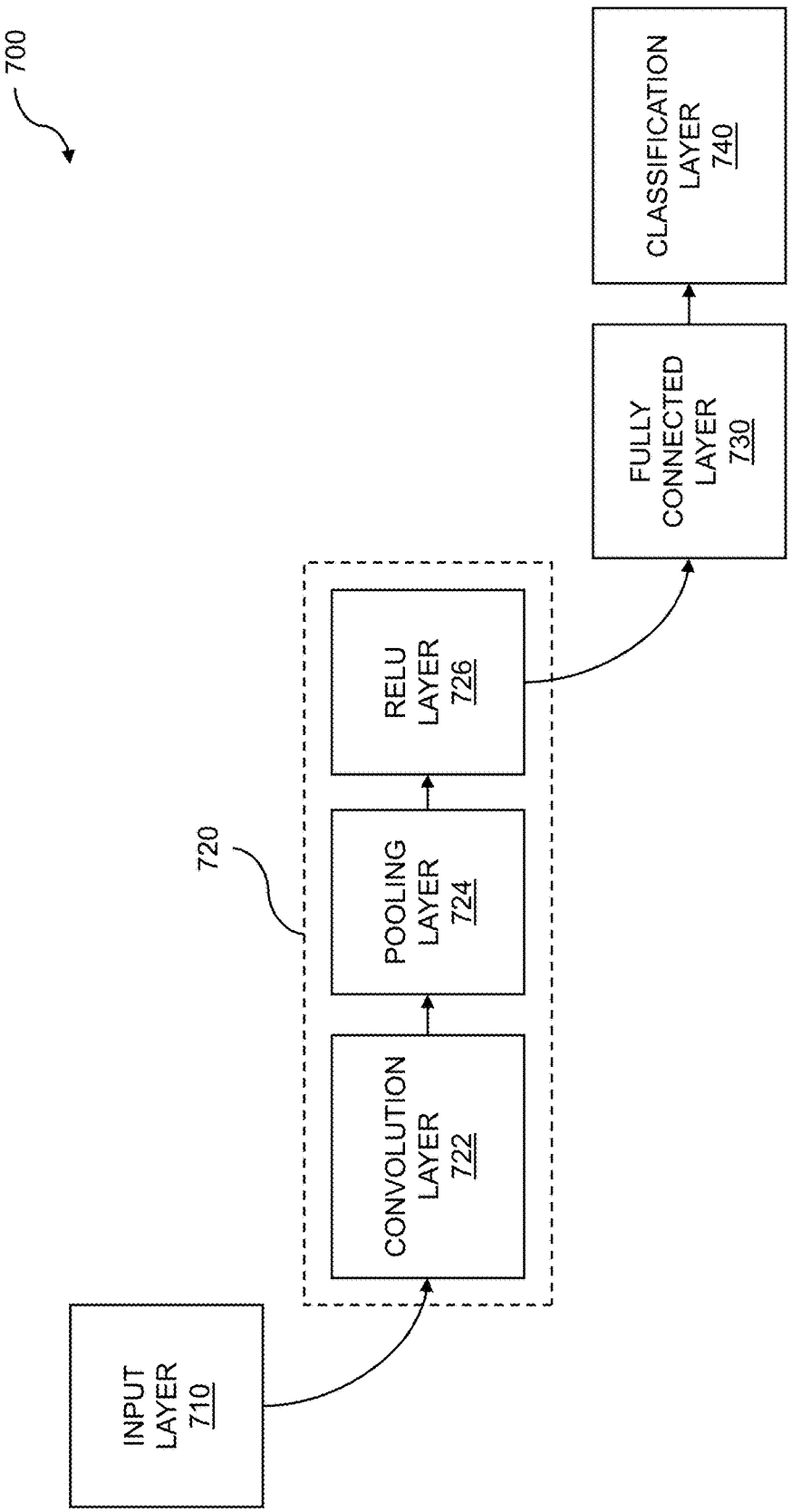
FIG. 7 is an example showing a convolutional neural network (CNN).

FIG. 7 is an example showing a convolutional neural network (CNN). A convolutional neural network such as 700 can be used for deep learning, where the deep learning can be applied to vehicle content recommendation using cognitive states. Images which include facial data are obtained from a vehicle occupant by using imaging devices. Other data can be obtained including audio data and physiological data. A content ingestion history including audio or video selections is obtained from the vehicle occupant. The images are analyzed to determine a cognitive state, and the cognitive state is correlated to the content ingestion history. Further audio or video selections are recommended to the vehicle occupant, based on the cognitive state, the content ingestion history, and the correlating. The convolutional neural network can be applied to analysis tasks such as cognitive state analysis, mental state analysis, mood analysis, emotional state analysis, and so on. The CNN can be applied to recommendation tasks such as vehicle content recommendation. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to act to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 7 is an example showing a convolutional neural network 700. The convolutional neural network can be used for deep learning, where the deep learning can be applied to cognitive state based vehicle manipulation using near-infrared image processing. The deep learning system can be accomplished using a convolution neural network or other techniques. The deep learning can accomplish facial recognition and analysis tasks. The network includes an input layer 710. The input layer 710 receives image data. The image data can be input in a variety of formats, such as JPEG, TIFF, BMP, and GIF. Compressed image formats can be decompressed into arrays of pixels, wherein each pixel can include an RGB tuple. The input layer 710 can then perform processing such as identifying boundaries of the face, identifying landmarks of the face, extracting features of the face, and/or rotating a face within the plurality of images.

The network includes a collection of intermediate layers 720. The multilayered analysis engine can include a convolutional neural network. Thus, the intermediate layers can include a convolution layer 722. The convolution layer 722 can include multiple sublayers, including hidden layers within it. The output of the convolution layer 722 feeds into a pooling layer 724. The pooling layer 724 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 724. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 726. The output of the pooling layer 724 can be input to the RELU layer 726. In embodiments, the RELU layer implements an activation function such as $f(x)$–$\max(0,x)$, thus providing an activation with a threshold at zero. In some embodiments, the RELU layer 726 is a leaky RELU layer. In this case, instead of the activation function providing zero when $x<0$, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 722 and one or more hidden layers, and wherein the multilayered analysis engine can be used for emotional analysis.

The example 700 includes a fully connected layer 730. The fully connected layer 730 processes each pixel/data point from the output of the collection of intermediate layers 720. The fully connected layer 730 takes all neurons in the previous layer and connects them to every single neuron it has. The output of the fully connected layer 730 provides input to a classification layer 740. The output of the classification layer 740 provides a facial expression and/or cognitive state as its output. Thus, a multilayered analysis engine such as the one depicted in FIG. 7 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 8:
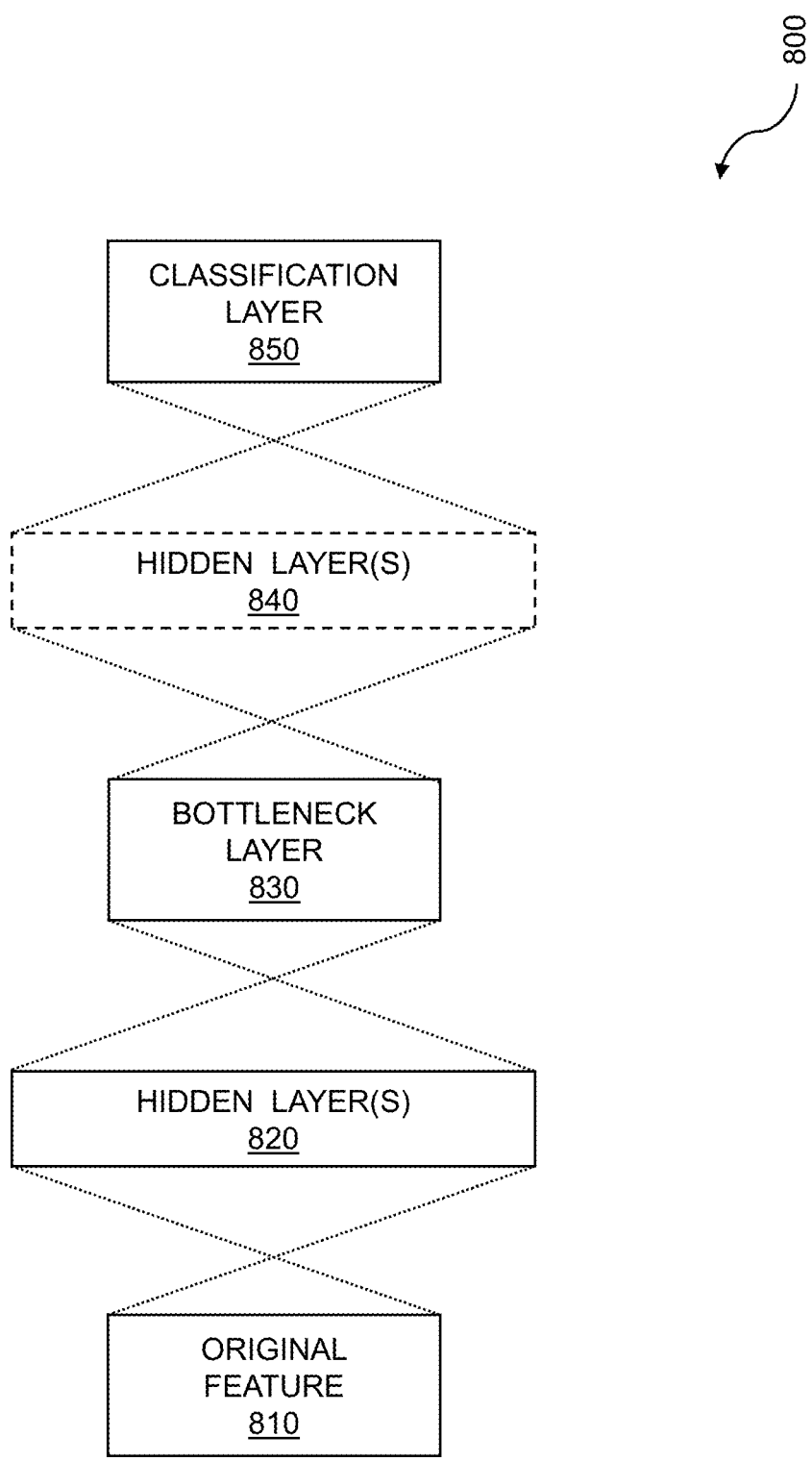
FIG. 8 illustrates a bottleneck layer within a deep learning environment.

FIG. 8 illustrates a bottleneck layer within a deep learning environment. A plurality of layers in a deep neural network (DNN) can include a bottleneck layer. The bottleneck layer can be used for vehicle content recommendation using cognitive states. A deep neural network can apply classifiers such as image classifiers, facial classifiers, audio classifiers, speech classifiers, physiological classifiers, and so on. The classifiers can be learned by analyzing cognitive state data. Images of a vehicle occupant are obtained, where the images include facial data. Content ingestion history is obtained, where the history includes audio or video selections. A first computing device is used to analyze the images to determine a cognitive state, and the cognitive state is correlated to the content ingestion history using a second computing device. Further audio or video selections are recommended to the vehicle occupant based on the cognitive state, the content ingestion history, and the correlating.

Layers of a deep neural network can include a bottleneck layer 800. A bottleneck layer can be used for a variety of applications such as facial recognition, voice recognition, emotional state recognition, and so on. The deep neural network in which the bottleneck layer is located can include a plurality of layers. The plurality of layers can include an original feature layer 810. A feature such as an image feature can include points, edges, objects, boundaries between and among regions, properties, and so on. The deep neural network can include one or more hidden layers 820. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 830. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 840. The number of the hidden layers can include zero hidden layers, one hidden layer, a plurality of hidden layers, and so on. The hidden layers following the bottleneck layer can include more nodes than the bottleneck layer. The deep neural network can include a classification layer 850. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 9:
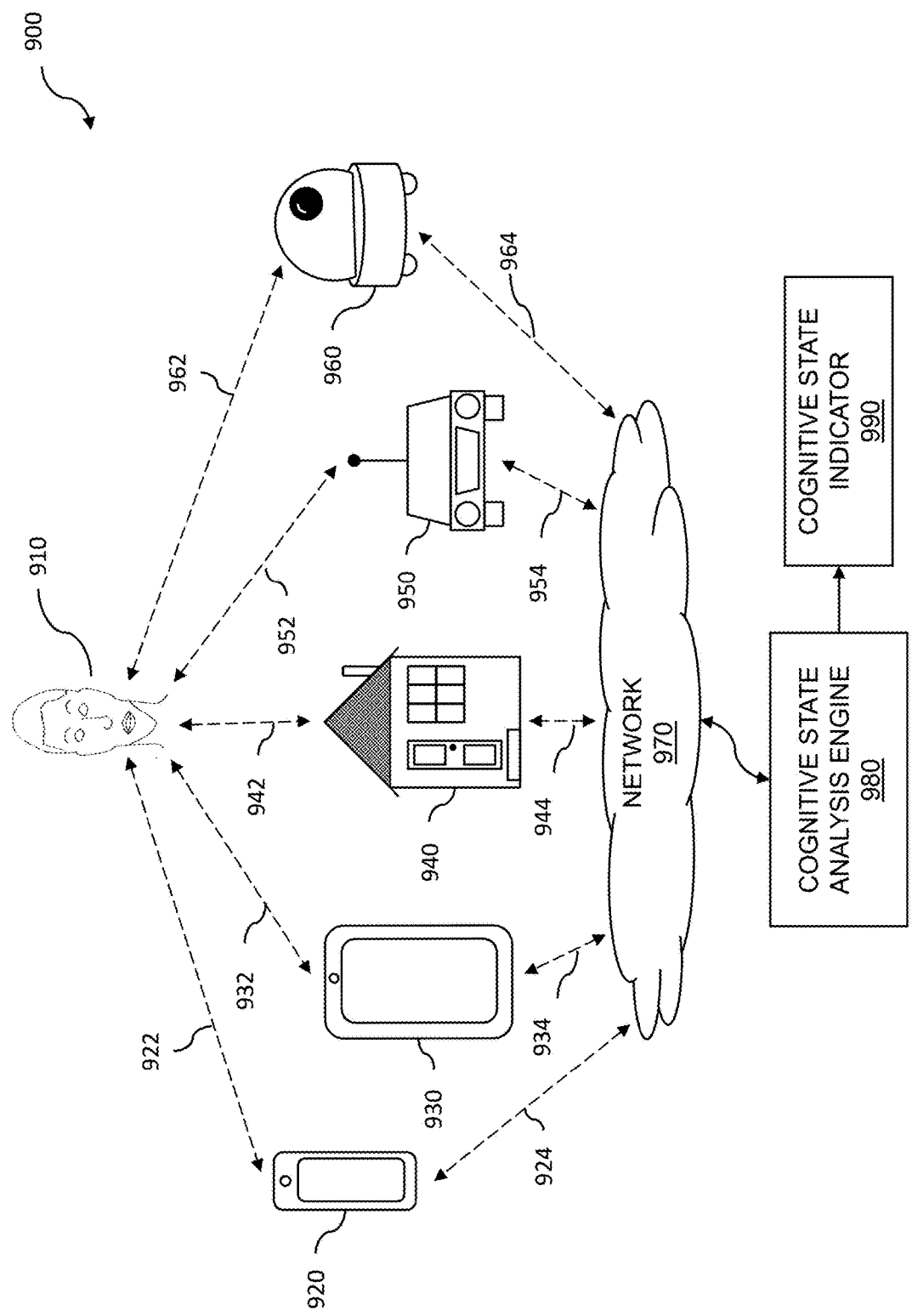
FIG. 9 shows data collection including devices and locations.

FIG. 9 shows data collection including devices and locations 900. Data, including video data, audio data and physio data, can be obtained for vehicle content recommendation using cognitive states. The data can be obtained from multiple devices, vehicles, and locations. Images including facial data of a vehicle occupant are obtained using imaging devices. The images can include visible light based images and near-infrared based images. Content ingestion history of the vehicle occupant is obtained. The ingestion history can include audio or video content. A first computing device is used to analyze the images to determine cognitive state. The cognitive state is correlated to the content ingestion history using a second computing device. Further audio or video selections are recommended to the vehicle occupant, based on the cognitive state, the content ingestion history, and the correlating.

The multiple mobile devices, vehicles, and locations 900 can be used separately or in combination to collect video data on a user 910. The video data can include facial data. Other data such as audio data, physiological data, and so on, can be collected on the user. While one person is shown, the video data, or other data, can be collected on multiple people. A user 910 can be observed as she or he is performing a task, experiencing an event, viewing a media presentation, and so on. The user 910 can be shown one or more media presentations, political presentations, social media, or another form of displayed media. The one or more media presentations can be shown to a plurality of people. The media presentations can be displayed on an electronic display coupled to a client device. The data collected on the user 910 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 910 can be analyzed and viewed for a variety of purposes including expression analysis, mental state analysis, cognitive state analysis, and so on. The electronic display can be on a smartphone 920 as shown, a tablet computer 930, a personal digital assistant, a television, a mobile monitor, or any other type of electronic device. In one embodiment, expression data is collected on a mobile device such as a cell phone 920, a tablet computer 930, a laptop computer, or a watch. Thus, the multiple sources can include at least one mobile device, such as a phone 920 or a tablet 930, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 910, data can be collected in a house 940 using a web camera or the like; in a vehicle 950 using a web camera, client device, etc.; by a social robot 960, and so on.

As the user 910 is monitored, the user 910 might move due to the nature of the task, boredom, discomfort, distractions, or for another reason. As the user moves, the camera with a view of the user's face can be changed. Thus, as an example, if the user 910 is looking in a first direction, the line of sight 922 from the smartphone 920 is able to observe the user's face, but if the user is looking in a second direction, the line of sight 932 from the tablet 930 is able to observe the user's face. Furthermore, in other embodiments, if the user is looking in a third direction, the line of sight 942 from a camera in the house 940 is able to observe the user's face, and if the user is looking in a fourth direction, the line of sight 952 from the camera in the vehicle 950 is able to observe the user's face. If the user is looking in a fifth direction, the line of sight 962 from the social robot 960 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 910 can also use a wearable device including a camera for gathering contextual information and/or collecting expression data on other users. Because the user 910 can move her or his head, the facial data can be collected intermittently when she or he is looking in a direction of a camera. In some cases, multiple people can be included in the view from one or more cameras, and some embodiments include filtering out faces of one or more other people to determine whether the user 910 is looking toward a camera. All or some of the expression data can be continuously or sporadically available from the various devices and other devices.

The captured video data can include cognitive content, such as facial expressions, etc., and can be transferred over a network 970. The network can include the Internet or other computer network. The smartphone 920 can share video using a link 924, the tablet 930 using a link 934, the house 940 using a link 944, the vehicle 950 using a link 954, and the social robot 960 using a link 964. The links 924, 934, 944, 954, and 964 can be wired, wireless, and hybrid links. The captured video data, including facial expressions, can be analyzed on a cognitive state analysis engine 980, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 990. The cognitive state indicator 990 can indicate cognitive states, mental states, moods, emotions, etc. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 10:
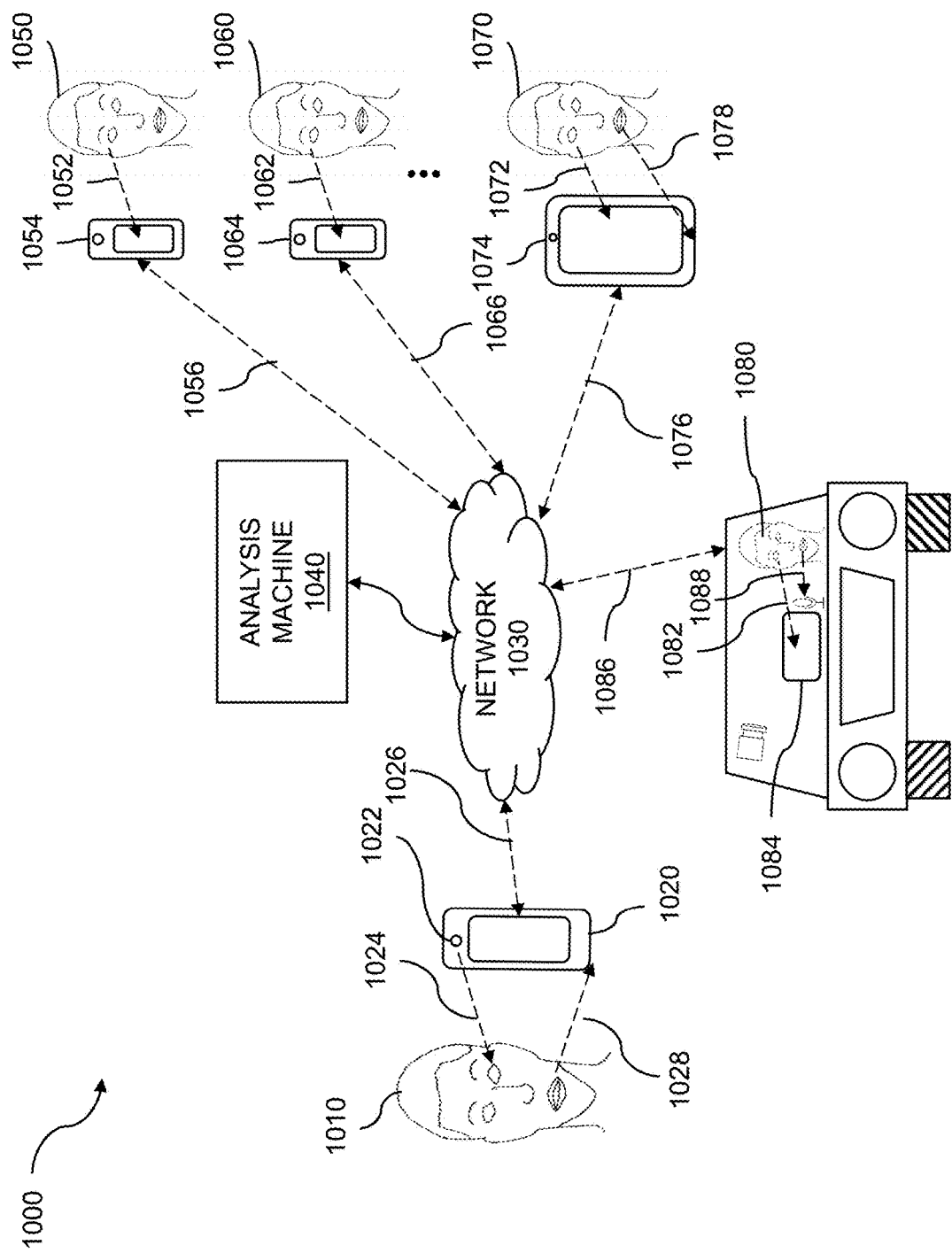
FIG. 10 illustrates an example of live streaming of social video and audio.

FIG. 10 shows an example of live streaming of social video and audio. The streaming of social video and social audio can be applied to vehicle content recommendation using cognitive states. The live streaming can include cognitive state data, image data, facial data, speech data, audio data, etc. Images of a vehicle occupant are obtained using one or more imaging devices within a vehicle, where the one or more images include facial data of the vehicle occupant. A content ingestion history of the vehicle occupant is obtained, where the content ingestion history includes one or more audio or video selections. A first computing device is used to analyze the one or more images to determine a cognitive state of the vehicle occupant. The cognitive state is correlated to the content ingestion history using a second computing device. One or more further audio or video selections are recommended to the vehicle occupant based on the cognitive state, the content ingestion history, and the correlating.

The live streaming and image analysis 1000 can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desired. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1000 shows a user 1010 broadcasting a video live stream and an audio live stream to one or more people as shown by a first person 1050, a second person 1060, and a third person 1070. A portable, network-enabled, electronic device 1020 can be coupled to a front-side camera 1022. The portable electronic device 1020 can be a smartphone, a PDA, a tablet, a laptop computer, and so on. The camera 1022 coupled to the device 1020 can have a line-of-sight view 1024 to the user 1010 and can capture video of the user 1010. The portable electronic device 1020 can be coupled to a microphone (not shown). The microphone can capture voice data 1028 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1040 using a network link 1026 to the network 1030. The network link can be a wireless link, a wired link, and so on. The recommendation engine 1040 can recommend to the user 1010 an app and/or platform that can be supported by the server and can be used to provide a video live stream, an audio live stream, or both a video live stream and an audio live stream to one or more followers of the user 1010.

In the example 1000, the user 1010 has four followers: a first person 1050, a second person 1060, a third person 1070, and a fourth person 1080. Each follower has a line-of-sight view to a video screen on a portable, networked electronic device. In other embodiments, one or more followers follow the user 1010 using any other networked electronic device, including a computer. In the example 1000, a first person 1050 has a line-of-sight view 1052 to the video screen of a device 1054; a second person 1060 has a line-of-sight view 1062 to the video screen of a device 1064, a third person 1070 has a line-of-sight view 1072 to the video screen of a device 1074, and a fourth person 1080 has a line-of-sight view 1082 to the video screen of a device 1084. The device 1074 can also capture audio data 1078 from the third person 1070, and the device 1084 can further capture audio data 1088 from the fourth person 1080. The portable electronic devices 1054, 1064, 1074, and 1084 can each be a smartphone, a PDA, a tablet, and so on. Each portable device can receive the video stream and the audio stream being broadcast by the user 1010 through the network 1030 using the app and/or platform that can be recommended by the recommendation engine 1040. The network can include the Internet, a computer network, a cellular network, and the like. The device 1054 can receive a video stream and the audio stream using the network link 1056, the device 1064 can receive a video stream and the audio stream using the network link 1066, the device 1074 can receive a video stream and the audio stream using the network link 1076, the device 1084 can receive a video stream and the audio stream using the network link 1086, and so on. The network link can be a wireless link, a wired link, a hybrid link, and the like. Depending on the app and/or platform that can be recommended by the analysis engine 1040, one or more followers, such as the followers shown 1050, 1060, 1070, and 1080, can reply to, comment on, or otherwise provide feedback to the user 1010 using their respective devices 1054, 1064, 1074, and 1084.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occlude or obscure the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 11:
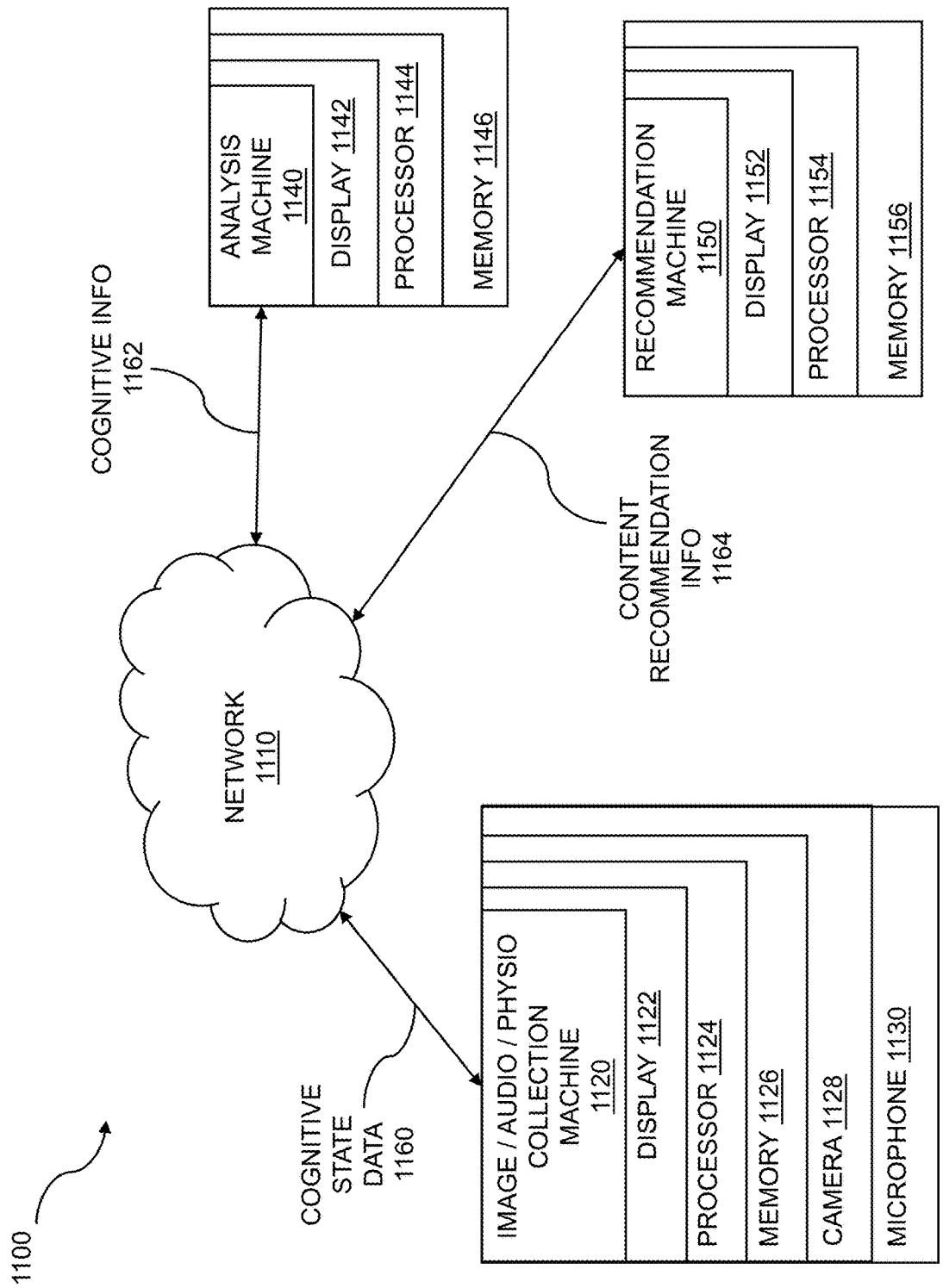
FIG. 11 is a diagram of a system for content manipulation using cognitive states.

FIG. 11 is a diagram of a system for content manipulation using cognitive states. Cognitive states can be used for vehicle content recommendation, where the recommendation uses analysis of images, audio data, or physiological data. Images are obtained of a vehicle occupant using one or more imaging devices within a vehicle. The one or more images include facial data of the vehicle occupant. Content ingestion history of the vehicle occupant is obtained, where the content ingestion history includes one or more audio or video selections. A first computing device is used to analyze the images to determine a cognitive state of the vehicle occupant. The cognitive state is correlated to the content ingestion history using a second computing device. One or more further audio or video selections are recommended to the vehicle occupant, based on the cognitive state, the content ingestion history, and the correlating. Audio information can be obtained from the occupant of the vehicle and can augment the analyzing based on the audio information. Physiological information can be obtained from the occupant of the vehicle and can augment the analyzing based on the physiological information.

The system 1100 can include a network 1110 (Internet, intranet, or another computer network), which can be used for communication among various machines. An image, audio, or physio collection machine 1120 has a memory 1126 which stores instructions and one or more processors 1124 attached to the memory 1126, wherein the one or more processors 1124 can execute instructions. The image, audio, or physio collection machine 1120 can also have a network connection to carry cognitive state data 1160, and a display 1122 that can present cognitive state data, cognitive state profiles, mental state data, mental state profiles, emotional states, emotional state profiles, and so on. The image, audio, or physio collection machine 1120 can collect cognitive state data including image data, facial data, voice data, audio data, physiological data, etc., from an occupant of a vehicle. In some embodiments, there are multiple image, audio, or physio collection machines 1120 that each collect cognitive state data including facial data. This type of collection machine can have a camera 1128, a microphone 1130, or other sensors. In many embodiments, a camera, a microphone, or physiological sensors will be present. Other embodiments include obtaining audio information and augmenting the analyzing of the cognitive state data with the audio information. The audio data can include speech, non-speech vocalizations, etc. Further embodiments may include obtaining physiological information from the occupant of the vehicle and augmenting the analyzing based on the physiological information. The physiological data can include heart rate, heart rate variability, respiration rate, skin conductivity, and so on. Once the cognitive state data 1160 has been collected, the image, audio, or physio collection machine 1120 can upload information to an analysis machine 1140, based on the cognitive state data from the occupant of the vehicle. The image, audio, or physio collection machine 1120 can communicate with the analysis machine 1140 over the network 1110, the Internet, some other computer network, or by another method suitable for communication between two machines. In some embodiments, the analysis machine 1140 functionality is embodied in the image and audio collection machine 1120.

The analysis machine 1140 can have a network connection for cognitive states or cognitive state information 1162, a memory 1146 which stores instructions, and one or more processors 1144 attached to the memory 1146, wherein the one or more processors 1144 can execute instructions. The analysis machine 1140 can receive cognitive state information, collected from an occupant of the vehicle, from the image, audio, or physio collection machine 1120, and can determine a cognitive state of the occupant. The analysis machine 1140 can also compare further cognitive state data with the cognitive state profile while the occupant is in a second vehicle. In some embodiments, the analysis machine 1140 also allows a user to view and evaluate the cognitive state data or other data for the occupant of the vehicle on a display 1142. The analysis machine 1140 can then provide the cognitive state information 1162 to the recommendation machine 1150. In some embodiments, the image, audio, or physio capture machine 1120 can also function as the recommendation machine 1150. In further embodiments, the cognitive state data that was analyzed can be based on intermittent obtaining of images that include facial data.

The recommendation machine 1150 can have a memory 1156 which stores instructions, and one or more processors 1154 attached to the memory 1156, wherein the one or more processors 1154 can execute instructions. The recommendation machine can use a computer network 1110, the Internet, or another computer communication method, to request the cognitive state information 1162 from the analysis machine. The recommendation machine 1150 can receive content recommendation information 1164, based on the cognitive state data 1160, from the occupant of the vehicle. The cognitive state information and vehicle content recommendation information for the occupant can be presented on a display 1152. In some embodiments, the recommendation machine is set up to receive cognitive state data collected from an occupant of the vehicle, in a real-time or near real-time embodiment. In other embodiments, the recommendation machine is set up to receive the cognitive state data on an intermittent basis. In at least one embodiment, a single computer incorporates the image, audio, or physio collection machine, the analysis machine, and the recommendation machine functionalities.

The system 1100 can comprise a computer system for content manipulation comprising: a memory which stores instructions; one or more processors attached to the memory wherein the one or more processors, when executing the instructions which are stored, are configured to: obtain one or more images of a vehicle occupant using one or more imaging devices within a vehicle, wherein the one or more images include facial data of the vehicle occupant; obtain a content ingestion history of the vehicle occupant, wherein the content ingestion history includes one or more audio or video selections; analyze, using a first computing device, the one or more images to determine a cognitive state of the vehicle occupant; correlate the cognitive state to the content ingestion history using a second computing device; and recommend to the vehicle occupant one or more further audio or video selections, based on the cognitive state, the content ingestion history, and the correlating.

In embodiments, a computer program product embodied in a non-transitory computer readable medium for content manipulation, the computer program product comprising code which causes one or more processors to perform operations of: obtaining one or more images of a vehicle occupant using one or more imaging devices within a vehicle, wherein the one or more images include facial data of the vehicle occupant; obtaining a content ingestion history of the vehicle occupant, wherein the content ingestion history includes one or more audio or video selections; analyzing, using a first computing device, the one or more images to determine a cognitive state of the vehicle occupant; correlating the cognitive state to the content ingestion history using a second computing device; and recommending to the vehicle occupant one or more further audio or video selections, based on the cognitive state, the content ingestion history, and the correlating.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples but is to be understood in the broadest sense allowable by law.

What is claimed is:

1. A computer-implemented method for content manipulation comprising:
    obtaining one or more images of a vehicle occupant using one or more imaging devices within a vehicle, wherein the one or more images include facial data of the vehicle occupant;
    obtaining a content ingestion history of the vehicle occupant, wherein the content ingestion history includes one or more audio or video selections;
    analyzing, using a first computing device, the one or more images to determine a cognitive state of the vehicle occupant;
    correlating the cognitive state to the content ingestion history using a second computing device; and
    recommending to the vehicle occupant one or more further audio or video selections, based on the cognitive state, the content ingestion history, and the correlating.

2. The method of claim 1 wherein the recommending occurs while the vehicle occupant occupies the vehicle.

3. The method of claim 1 wherein the recommending occurs after the vehicle occupant leaves the vehicle.

4. The method of claim 1 further comprising comparing the analyzing with additional analyzing performed on additional vehicle occupants.

5. The method of claim 4 wherein the additional vehicle occupants occupy the vehicle contemporaneously with the vehicle occupant.

6. The method of claim 4 wherein the additional vehicle occupants occupy one or more different vehicles from the vehicle of the vehicle occupant.

7. The method of claim 1 further comprising obtaining additional images of one or more additional occupants of the vehicle, wherein the additional images are analyzed to determine one or more additional cognitive states.

8. The method of claim 7 further comprising adjusting the correlating the cognitive state, wherein the adjusting is performed using the additional cognitive states.

9. The method of claim 8 further comprising changing the recommending based on the adjusting.

10. The method of claim 8 wherein the vehicle occupant and the one or more additional occupants comprise a group of occupants and the adjusting is performed based on a group cognitive state.

11. The method of claim 1 wherein the analyzing is performed without eye region input from the one or more images.

12. The method of claim 1 wherein the vehicle occupant is a driver of the vehicle.

13. The method of claim 12 wherein the driver is a custodial driver.

14. The method of claim 1 further comprising obtaining audio information from the vehicle occupant and augmenting the analyzing based on the audio information.

15. The method of claim 14 wherein the audio information includes speech.

16. The method of claim 14 wherein the audio information includes non-speech vocalizations.

17. The method of claim 16 wherein the non-speech vocalizations include grunts, yelps, squeals, snoring, sighs, laughter, filled pauses, unfilled pauses, or yawns.

18. The method of claim 1 wherein the analyzing is performed using deep learning.

19. The method of claim 1 further comprising tagging the cognitive state with sensor data.

20. The method of claim 19 wherein the sensor data includes one or more of an interior temperature for the vehicle, an exterior temperature for the vehicle, a time of day, a day of week, a season, a level of daylight, weather conditions, road conditions, traffic conditions, a headlight activation, a windshield wiper activation, a setting for the vehicle, an entertainment center selection for the vehicle, or an entertainment center volume for the vehicle.

21. The method of claim 1 wherein at least one of the one or more images includes near infrared content.

22. The method of claim 21 wherein the analyzing is modified, based on the near infrared content of the at least one of the one or more images.

23. The method of claim 1 wherein the cognitive state includes drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

24. The method of claim 1 wherein the cognitive state that was analyzed is based on intermittent obtaining of the one or more images that include facial data.

25. A computer program product embodied in a non-transitory computer readable medium for content manipulation, the computer program product comprising code which causes one or more processors to perform operations of:

obtaining one or more images of a vehicle occupant using one or more imaging devices within a vehicle, wherein the one or more images include facial data of the vehicle occupant;

obtaining a content ingestion history of the vehicle occupant, wherein the content ingestion history includes one or more audio or video selections;

analyzing, using a first computing device, the one or more images to determine a cognitive state of the vehicle occupant;

correlating the cognitive state to the content ingestion history using a second computing device; and recommending to the vehicle occupant one or more further audio or video selections, based on the cognitive state, the content ingestion history, and the correlating.

26. A computer system for content manipulation comprising:

a memory which stores instructions;

one or more processors attached to the memory wherein the one or more processors, when executing the instructions which are stored, are configured to:

obtain one or more images of a vehicle occupant using one or more imaging devices within a vehicle, wherein the one or more images include facial data of the vehicle occupant;

obtain a content ingestion history of the vehicle occupant, wherein the content ingestion history includes one or more audio or video selections;

analyze, using a first computing device, the one or more images to determine a cognitive state of the vehicle occupant;

correlate the cognitive state to the content ingestion history using a second computing device; and recommend to the vehicle occupant one or more further audio or video selections, based on the cognitive state, the content ingestion history, and the correlating.

* * * * *